(12) United States Patent
Yamashita

(10) Patent No.: US 10,417,482 B2
(45) Date of Patent: Sep. 17, 2019

(54) OBSERVATION SYSTEM

(71) Applicant: OLYMPUS CORPORATION, Hachioji-shi, Tokyo (JP)

(72) Inventor: Yusuke Yamashita, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 109 days.

(21) Appl. No.: 15/844,441

(22) Filed: Dec. 15, 2017

(65) Prior Publication Data

US 2018/0204047 A1  Jul. 19, 2018

(30) Foreign Application Priority Data

Jan. 16, 2017 (JP) ................ 2017-005153

(51) Int. Cl.
| | |
|---|---|
| *G06K 9/00* | (2006.01) |
| *G06K 9/46* | (2006.01) |
| *G06T 7/55* | (2017.01) |
| *G06K 9/20* | (2006.01) |
| *C12M 1/34* | (2006.01) |
| *G16H 50/00* | (2018.01) |

(52) U.S. Cl.
CPC .......... *G06K 9/00147* (2013.01); *C12M 1/34* (2013.01); *C12M 41/36* (2013.01); *G06K 9/00127* (2013.01); *G06K 9/00134* (2013.01); *G06K 9/00201* (2013.01); *G06K 9/2081* (2013.01); *G06K 9/469* (2013.01); *G06T 7/55* (2017.01); *G16H 50/00* (2018.01); *G06K 2209/27* (2013.01); *G06T 2207/10056* (2013.01); *G06T 2207/10064* (2013.01)

(58) Field of Classification Search
USPC ..................................... 382/128, 132, 133
See application file for complete search history.

(56) References Cited

U.S. PATENT DOCUMENTS

| | | | |
|---|---|---|---|
| 9,588,033 B2 * | 3/2017 | Zahniser | G01N 15/1475 |
| 9,642,941 B2 * | 5/2017 | Witt | A61L 27/54 |
| 10,235,759 B2 * | 3/2019 | Kosmecki | G06T 7/149 |

(Continued)

FOREIGN PATENT DOCUMENTS

| | | |
|---|---|---|
| JP | 2010085420 A | 4/2010 |
| JP | 2011179924 A | 9/2011 |
| JP | 2016220613 A | 12/2016 |

*Primary Examiner* — Ishrat I Sherali

(74) *Attorney, Agent, or Firm* — Holtz, Holtz & Volek PC

(57) ABSTRACT

Provided is an observation system including: a monitor; a CPU that identifies, in a 3D image including the plurality of cells, the respective cells by assigning labels that differ from one another to the respective cells, that associates three mutually-intersecting cross-sectional images that constitute the 3D image, and that simultaneously displays the cross-sectional images on the monitor; and an input unit with which an operator specifies an arbitrary cell in any of the cross-sectional images displayed on the monitor. The CPU extracts, from the 3D image, the cross-sectional shapes, in the respective cross-sectional images, of the cell specified by using the input unit, on the basis of the labels, associates the extracted cross-sectional shapes of the cell with one another, and displays the extracted cross-sectional shapes in the respective cross-sectional images displayed on the monitor, in a distinguishable manner from the other cells.

20 Claims, 19 Drawing Sheets

(56) References Cited

U.S. PATENT DOCUMENTS

2006/0183992 A1* 8/2006 Kawashima ............. A61B 8/12
                                                        600/407
2010/0083410 A1   4/2010 Hattori et al.
2011/0212486 A1   9/2011 Yamada et al.
2019/0107528 A1*  4/2019 Yamashita ......... G01N 33/4833

* cited by examiner

FIG. 3

TABLE

| LABEL (OBJECT ID) | CENTER POSITION INFORMATION | BOUNDING RECTANGLE |
|---|---|---|
| 1 | (X1, Y1, Z1) | (X1_d, Y1_d, Z1_d) |
| 2 | (X2, Y2, Z2) | (X2_d, Y2_d, Z2_d) |
| 3 | (X3, Y3, Z3) | (X3_d, Y3_d, Z3_d) |
| 4 | (X4, Y4, Z4) | (X4_d, Y4_d, Z4_d) |
| ... | ... | ... |
| k | (Xk, Yk, Zk) | (Xk_d, Yk_d, Zk_d) |
| ... | ... | ... |
| n | (Xn, Yn, Zn) | (Xn_d, Yn_d, Zn_d) |

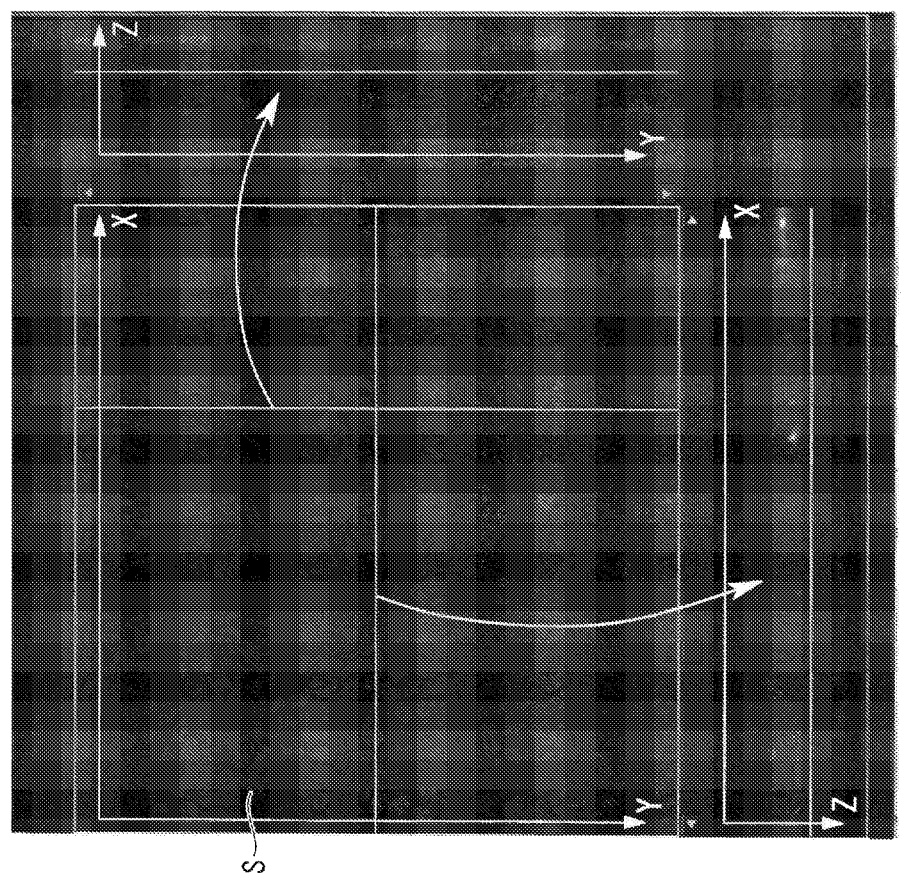
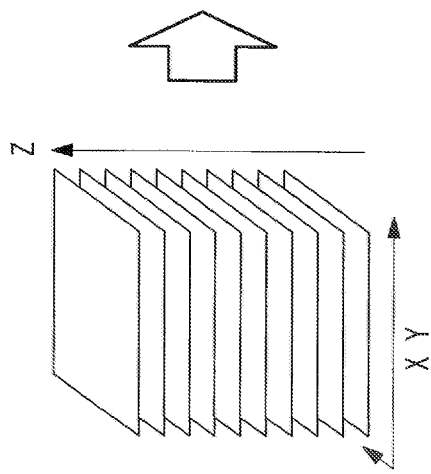
FIG. 4

FIG. 10
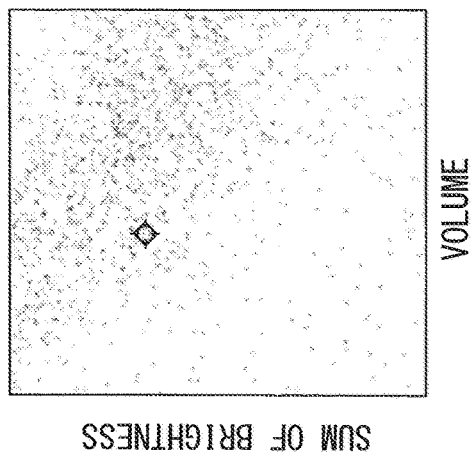
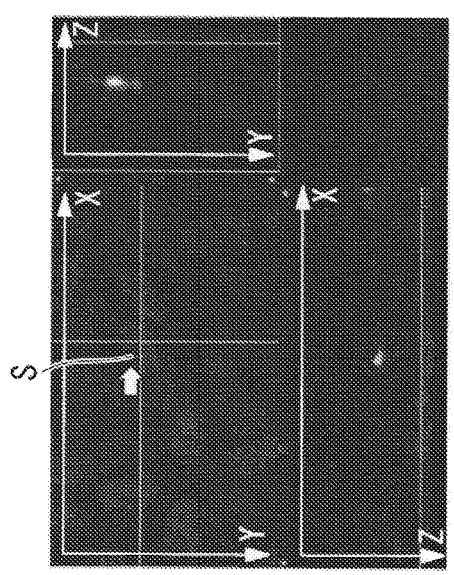
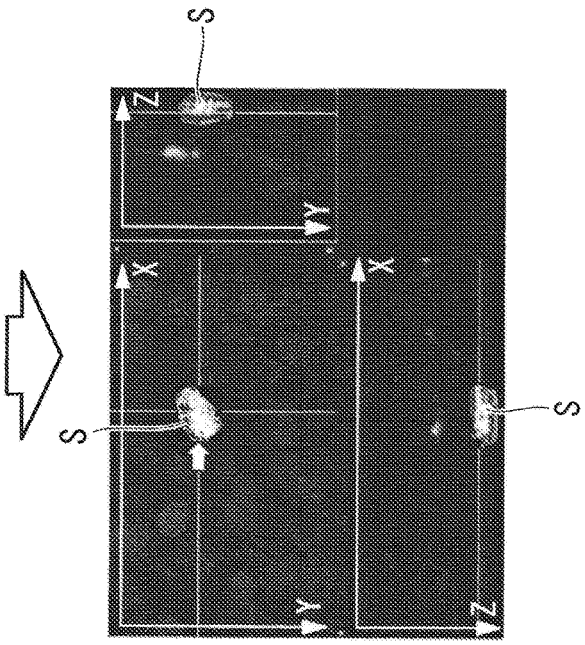

FIG. 14
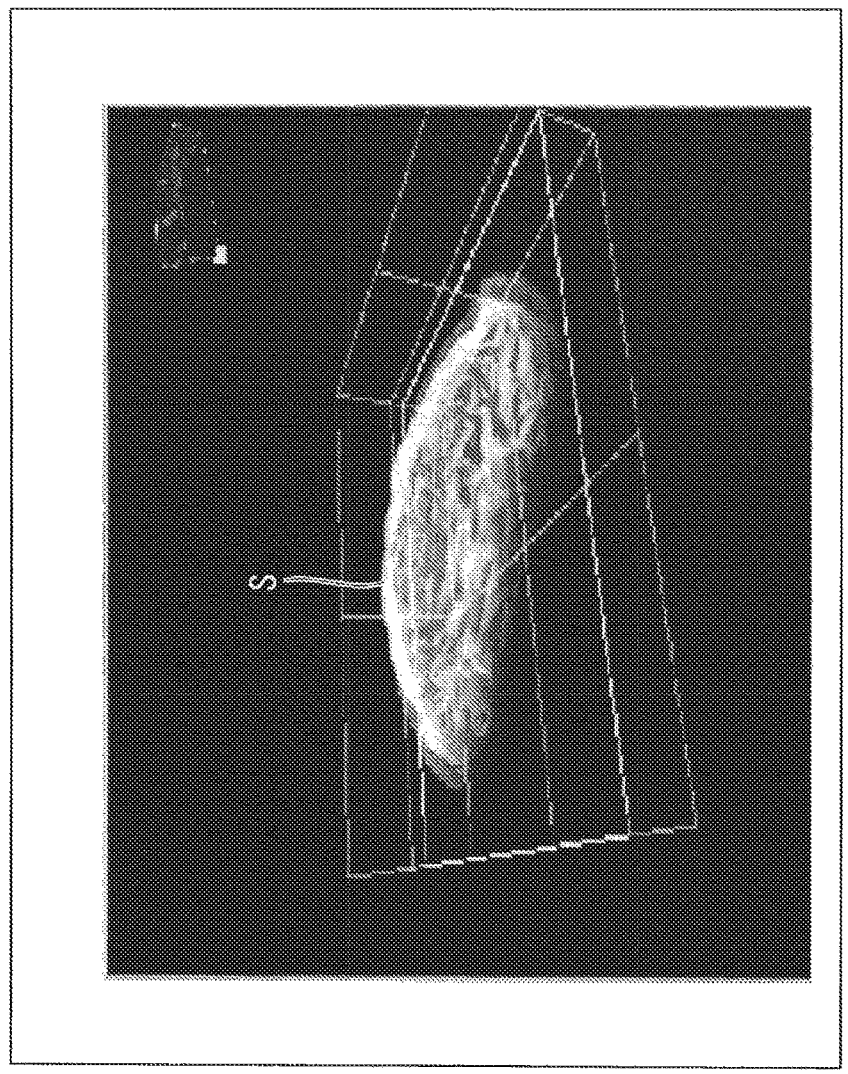
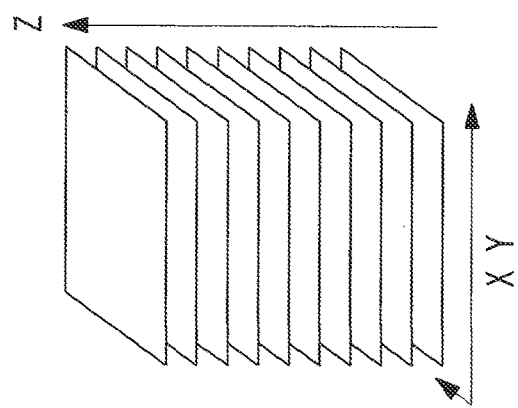

FIG. 16
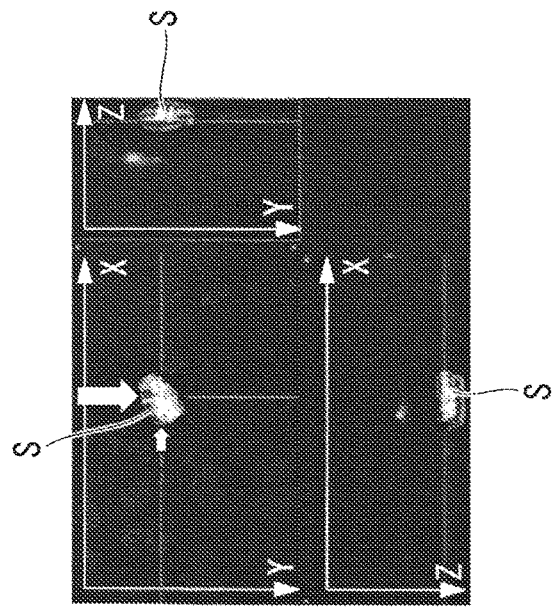
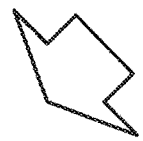
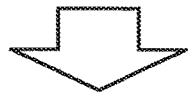
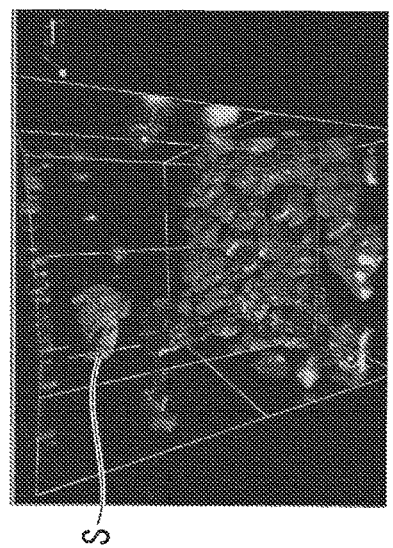
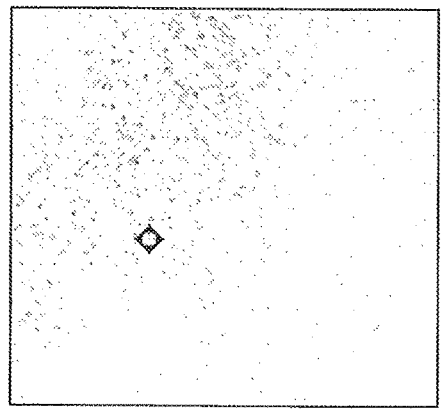

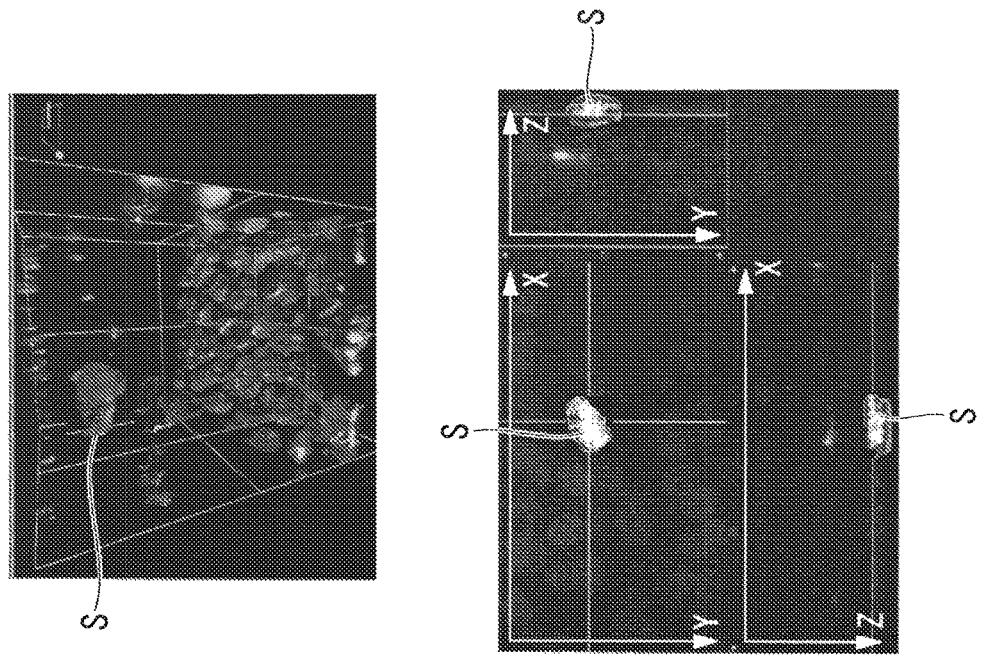
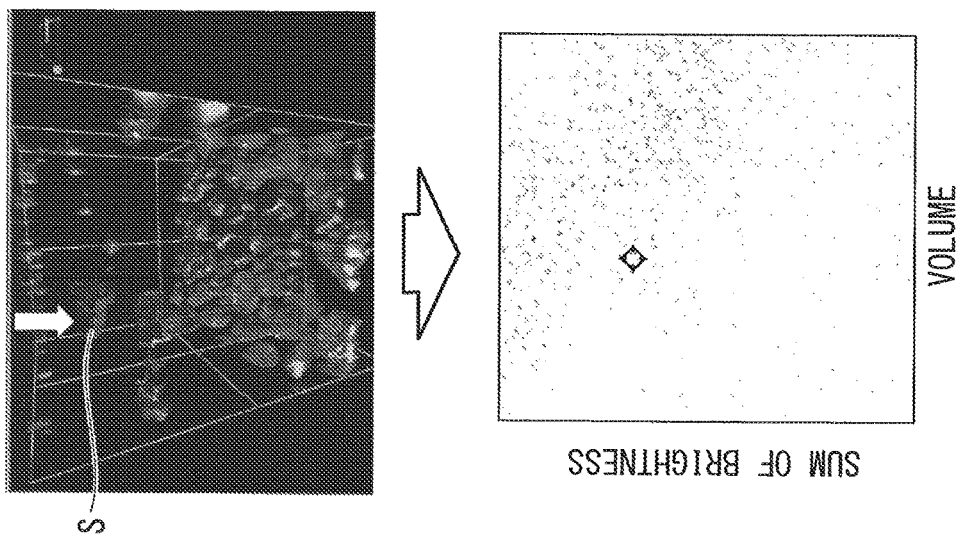
FIG. 18

OBSERVATION SYSTEM

CROSS-REFERENCE TO RELATED APPLICATIONS

This application is based on Japanese Patent Application No. 2017-005153, the contents of which are incorporated herein by reference.

The present invention relates to an observation system.

BACKGROUND ART

In the related art, there are known observation systems for observing, in 3D culturing in which cells are sterically cultured, the culture state of a cell clump etc. in which a plurality of cells are sterically collected and that has a 3D structure (for example, see PTL 1).

The observation system disclosed in PTL 1 recognizes, in a 2D fluorescence observation image, regions of cell components, such as cell clumps, nuclei, cell membrane, and cell cytoplasm, according to dyes, recognizes and extracts each target site from the 2D fluorescence observation image on the basis of the amount of the dyes, and outputs a measurement value, e.g., the area, of the target site. Furthermore, in order to determine the validity of recognition processing of the target site, the observation system disclosed in PTL 1 confirms both the shape of the target site recognized in the 2D fluorescence observation image and the distribution in a histogram obtained from an analysis result of the target site.

CITATION LIST

Patent Literature

{PTL 1} Japanese Unexamined Patent Application, Publication No. 2011-179924

SUMMARY OF INVENTION

According to one aspect, the present invention provides an observation system including: a display unit that displays an image of cells; a cell identifying unit that identifies, in a 3D image including the plurality of cells, the respective cells by assigning labels that differ from one another to the respective cells; a display control unit that associates three mutually-intersecting cross-sectional images that constitute the 3D image and that simultaneously displays the cross-sectional images on the display unit; a cell specifying unit with which an operator specifies an arbitrary one of the cells in any of the cross-sectional images, which are displayed on the display unit by the display control unit; and a cross-sectional-shape extracting unit that extracts, from the 3D image, cross-sectional shapes, in the respective cross-sectional images, of the cell specified by using the cell specifying unit, on the basis of the labels assigned to the respective cells, wherein the display control unit associates the cross-sectional shapes of the cell, which are extracted by the cross-sectional-shape extracting unit, with one another and displays the cross-sectional shapes of the cell in the respective cross-sectional images displayed on the display unit, in a distinguishable manner from the other cells.

BRIEF DESCRIPTION OF DRAWINGS

FIG. 3 is a view showing an example table.

FIG. 4 is a view showing a state in which an XY cross-sectional image, an XZ cross-sectional image, and a YZ cross-sectional image are displayed next to one another on a monitor.

FIG. 10 is a view showing a state in which an arbitrary cell is specified in the XY cross-sectional image, thereby highlighting the cross-sectional shapes of the cell in the respective cross-sectional images and highlighting the value indicating the analysis result of the cell in the graph.

FIG. 14 is a view showing an example 3D image displayed on a monitor by an observation system according to a second embodiment of the present invention.

FIG. 16 is a view showing a state in which an arbitrary cell is specified in the XY cross-sectional image, thereby highlighting the respective cross-sectional shapes of the cell in the respective cross-sectional images, highlighting the 3D shape of the cell in the 3D image, and highlighting the value indicating the analysis result of the cell in the graph.

FIG. 18 is a view showing a state in which an arbitrary cell is specified in the 3D image, thereby highlighting the 3D shape of the cell in the 3D image, highlighting the respective cross-sectional shapes of the cell in the respective cross-sectional images, and highlighting the value indicating the analysis result of the cell in the graph.

DESCRIPTION OF EMBODIMENTS

First Embodiment

An observation system according to a first embodiment of the present invention will be described below with reference to the drawings.

Figure 1:
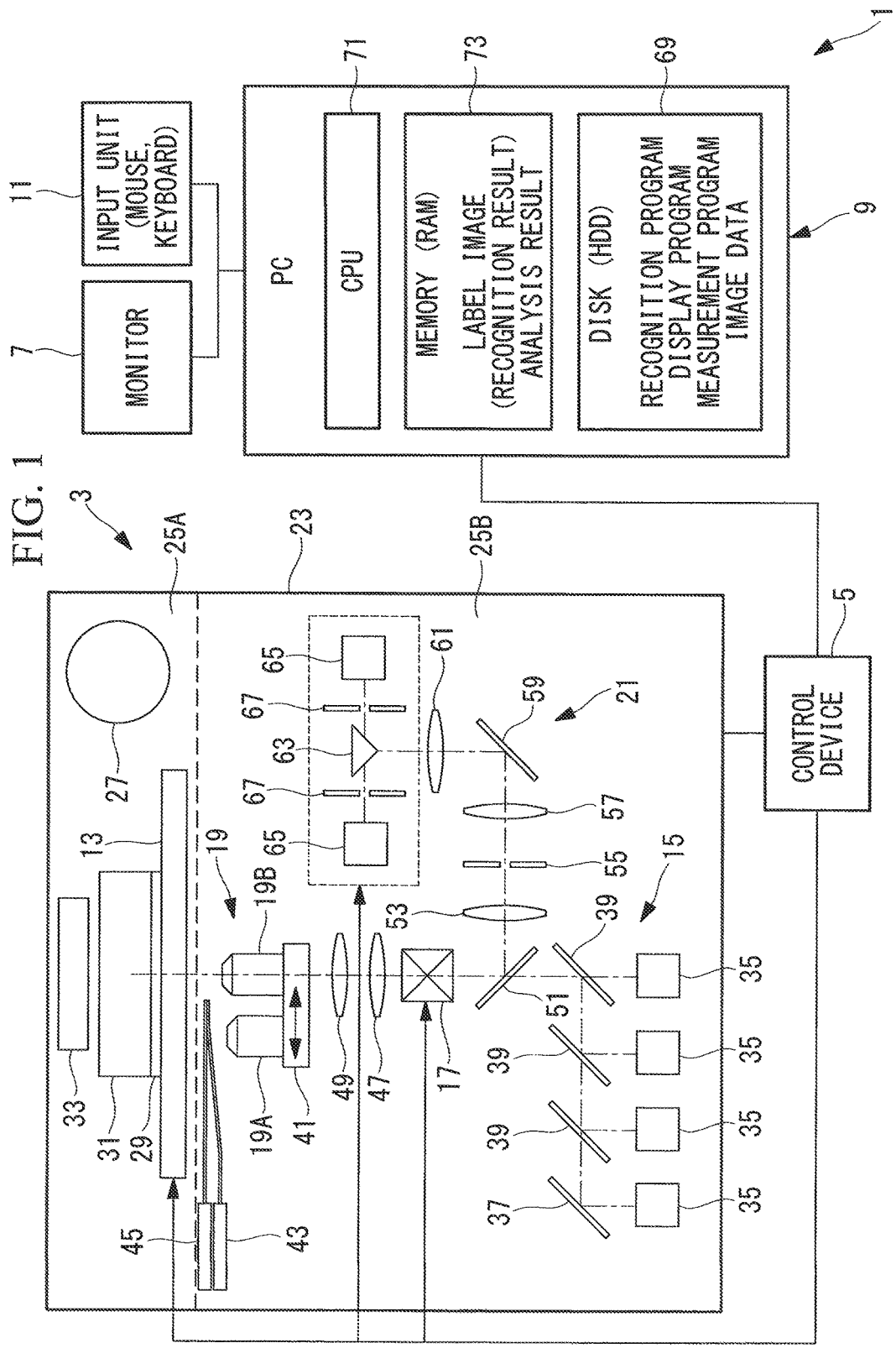
FIG. 1 is a view showing, in outline, the configuration of an observation system according to a first embodiment of the present invention.

As shown in FIG. 1, an observation system 1 of this embodiment is provided with a laser-scanning microscope 3, a control device 5 that controls the laser-scanning microscope 3 and that constructs an image, a monitor (display unit) 7 that displays the image constructed by the control device 5, a PC (Personal Computer) 9, and an input unit (cell specifying unit) 11, such as a mouse or a keyboard, with which an operator performs various types of input.

The laser-scanning microscope 3 is provided with: a motorized stage 13 that mounts, thereon, a transparent container (not shown), such as a petri dish, for accommodating spheroids (cell clumps), which are each composed of a plurality of cells S (see FIGS. 6 and 7); a laser-light source unit 15 that emits laser light; a scanner 17 that two-dimensionally scans the laser light emitted by the laser-light source unit 15; an objective lens 19 that focuses, on the cells S, the laser light scanned by the scanner 17; an image acquisition unit 21 that detects fluorescence produced in the cells S irradiated with the laser light via the objective lens 19 and that acquires an image of the cells S; and a dark box 23 that accommodates the above-described units etc.

The motorized stage 13 is provided with three motors (not shown) and independently moves along moving axes in mutually orthogonal X, Y, and Z directions, thus making it possible to move the container mounted thereon in the 3D directions.

The interior of the dark box 23 is partitioned into an upper region 25A that includes the motorized stage 13 and that is located on an upper side and a lower region 25B that is located lower than the upper region 25A. A heater 27 is disposed in the upper region 25A, so that the temperature of the interior of the upper region 25A is adjusted so as to become a predetermined culture condition (for example, 37° C.±0.5° C.). Furthermore, a sample holder 29 that is mounted in a positioned manner on the motorized stage 13 is disposed in the upper region 25A.

The sample holder 29 can hold the container in a positioned manner on the motorized stage 13. The container held by the sample holder 29 is accommodated inside a simple incubator 31, so that the culture conditions (for example, a humidity of 100% and a $CO_2$ concentration of 0.5%) thereof are maintained. In the figure, reference sign 33 denotes a phase difference condensor for phase difference observation.

The laser-light source unit 15 is provided with: a plurality of laser diodes 35 that produce laser light beams at different wavelengths; and a mirror 37 and dichroic mirrors 39 that merge the laser light beams produced by the plurality of laser diodes 35 into a single light path.

The scanner 17 is, for example, a so-called proximity galvanometer mirror that is configured such that two galvanometer mirrors that are made to swing about mutually orthogonal axes are opposed to each other.

The objective lens 19 is provided such that it is possible to switch between an objective lens 19A for dry observation and an objective lens 19B for oil-immersion or water-immersion observation, by a revolver 41. Furthermore, the objective lens 19 is provided with an autofocus function, detects a focus position periodically or as needed, and is moved in the direction along the optical axis, thereby making it possible to match the focus position of the objective lens 19 with the surface of the cells S.

In the figure, reference sign 43 denotes a pump for supplying immersion oil for oil immersion or water for water immersion between the objective lens 19B and the bottom surface of the container. In the figure, reference sign 45 denotes an airbrush for removing the water or the immersion oil.

A pupil projection lens 47 and an imaging lens 49 that focus the laser light scanned by the scanner 17 are disposed between the scanner 17 and the objective lens 19.

The image acquisition unit 21 is provided with: a beam splitter 51 that is inserted between the laser-light source unit 15 and the scanner 17 and that splits off, from the light path of the laser light, fluorescence that is produced in the cells S and that returns via the objective lens 19, the imaging lens 49, the pupil projection lens 47, and the scanner 17; a confocal lens 53 that focuses the fluorescence split off by the beam splitter 51; a variable pinhole 55; a collimating lens 57; a grating 59 that diffracts the fluorescence converted into substantially collimated light by the collimating lens 57, thus separating the fluorescence into respective wavelengths; a condensing lens 61 that condenses the fluorescence separated by the grating 59; a beam splitter 63 that splits the condensed fluorescence into respective wavelengths; and light detectors 65 that each detect the fluorescence split by the beam splitter 63. The variable pinhole 55 is disposed at a position that has an optically-conjugate positional relationship with the focus position of the objective lens 19. Reference sign 67 denotes pinholes.

The control device 5 controls driving of the motorized stage 13 and the scanner 17 and constructs an image on the basis of luminance information output from the light detectors 65. For example, the control device 5 three-dimensionally moves the motorized stage 13 with respect to the objective lens 19, thereby three-dimensionally moving the spheroid with respect to the focus position of the objective lens 19, and, while three-dimensionally moving the spheroid, causes the scanner 17 to two-dimensionally scan the laser light on each focus position, and constructs a slice image (acquired image) of the cells S disposed at the focus position of the objective lens 19 on the basis of luminance signals output from the light detectors 65 that have detected the fluorescence produced in the cells S, thereby acquiring a plurality of slice images of the respective cells S.

Then, the control device 5 processes the plurality of slice images of the respective cells S, thereby constructing a 3D image of the entire spheroid. Data of the plurality of slice images and the 3D image obtained by the control device 5 is sent to the PC 9.

The control device 5 is constituted by: a first communication I/F circuit (not shown) for performing data communication with the PC; a second communication I/F circuit (not shown) for performing data communication with the laser-scanning microscope 3 in order to control the motorized stage 13, the scanner 17, the light detectors 65, etc.; a CPU (not shown); a memory (not shown); and the like. Note that, in order to efficiently generate a 3D image, a GPU (Graphics Processing Unit, not shown) may be provided separately from the CPU.

The PC 9 is provided with: a disk (HDD: Hard Disk Drive) 69 that stores various programs, image data, graph data, etc.; a CPU (Central Processing Unit, cell identifying unit, display control unit, cell specifying unit, cross-sectional-shape extracting unit, analysis-result extracting unit) 71 that executes the programs stored in the disk 69; and a memory 73, such as a RAM (Random Access Memory), that stores recognition results and analysis results of the cells S, obtained through execution of the programs by the CPU 71.

The disk 69 stores, for example, a recognition program, a display program, and a measurement program, as the programs to be executed by the CPU 71. Furthermore, the disk 69 stores image data, such as a plurality of slice images of the respective cells S and a 3D image of the entire spheroid, obtained by the control device 5.

Through execution of the recognition program, the CPU 71 performs recognition processing for the entire spheroid and individual cells S in a 3D image. In the recognition processing, for example, a plurality of LoG (Laplacian Of Gaussian) filters having different sizes are adopted, a local peak position and the size thereof are detected from output values of the LoG filters, and this peak position is set as a seed (the center position of a cell S). Then, the LoG filters are two-dimensionally and three-dimensionally applied, and the results thereof are combined. Next, an area surrounding the seed is subjected to trimming and adaptively to binarization processing on the basis of the size of the area, thus forming an area of the recognized cell S.

Figure 2:
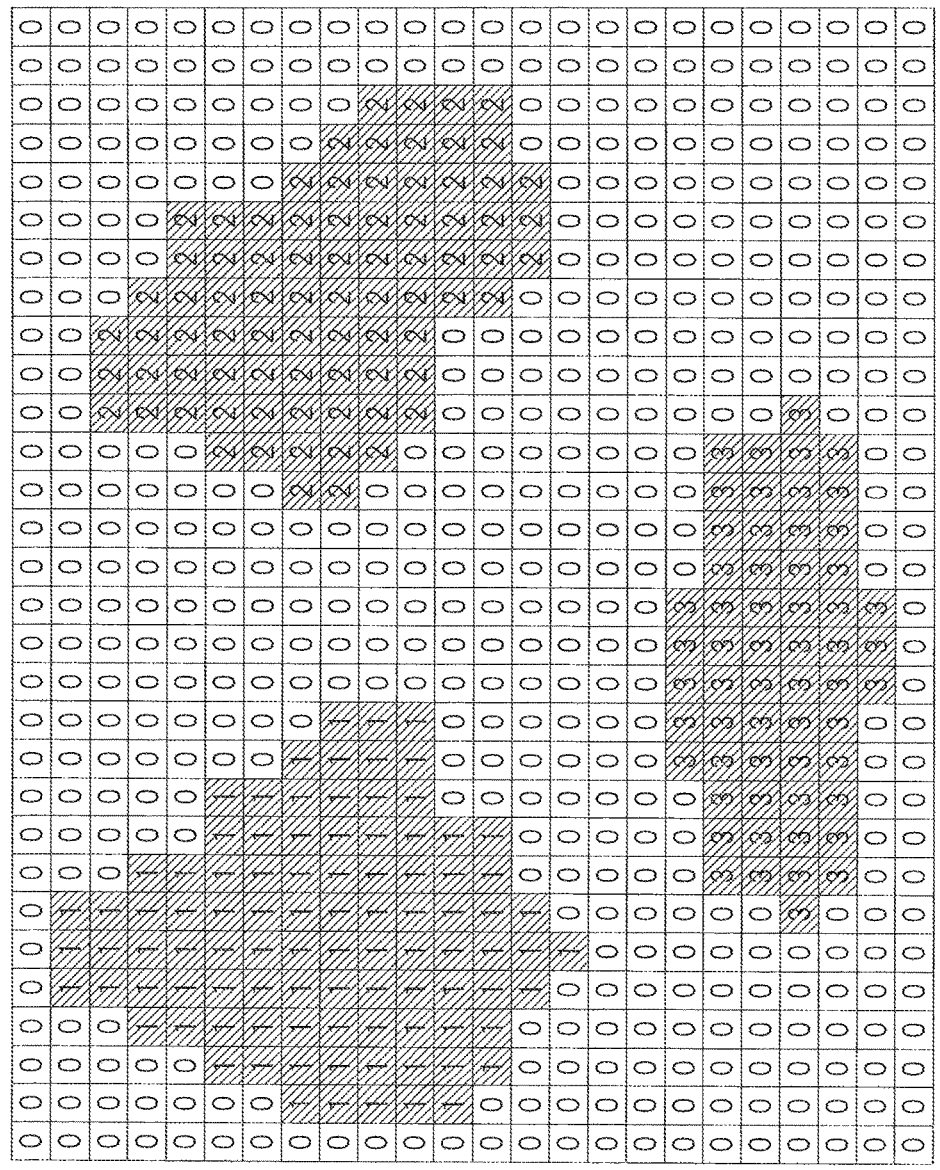
FIG. 2 is a view showing an example label image.

Furthermore, the CPU 71 identifies the recognized entire spheroid or individual recognized cells S by assigning different labels thereto and generates a label image, as shown in FIG. 2, and a table, as shown in FIG. 3, for example.

As shown in FIG. 2, the label image is a 2D image that shows objects and a background such that object IDs (for example, 1, 2, 3, 4, . . . k . . . n), serving as the labels, are assigned, to respective recognized objects, and 0 is assigned to the unrecognized background. The table is information in which the label (object ID), the center-position information, and the circumscribed rectangle are associated, as shown in FIG. 3. The label image and the table generated by the CPU 71 are stored in the memory 73.

Furthermore, through execution of the measurement program, the CPU 71 measures and analyzes the individual cells S, which constitute the spheroid recognized from the 3D image, and generates graphs showing characteristic distributions of the measured and analyzed cells S. The graphs can be, for example, a histogram, a scattergram, a line graph, etc. The graphs generated by the CPU 71 are stored in the disk 69.

Figure 5:
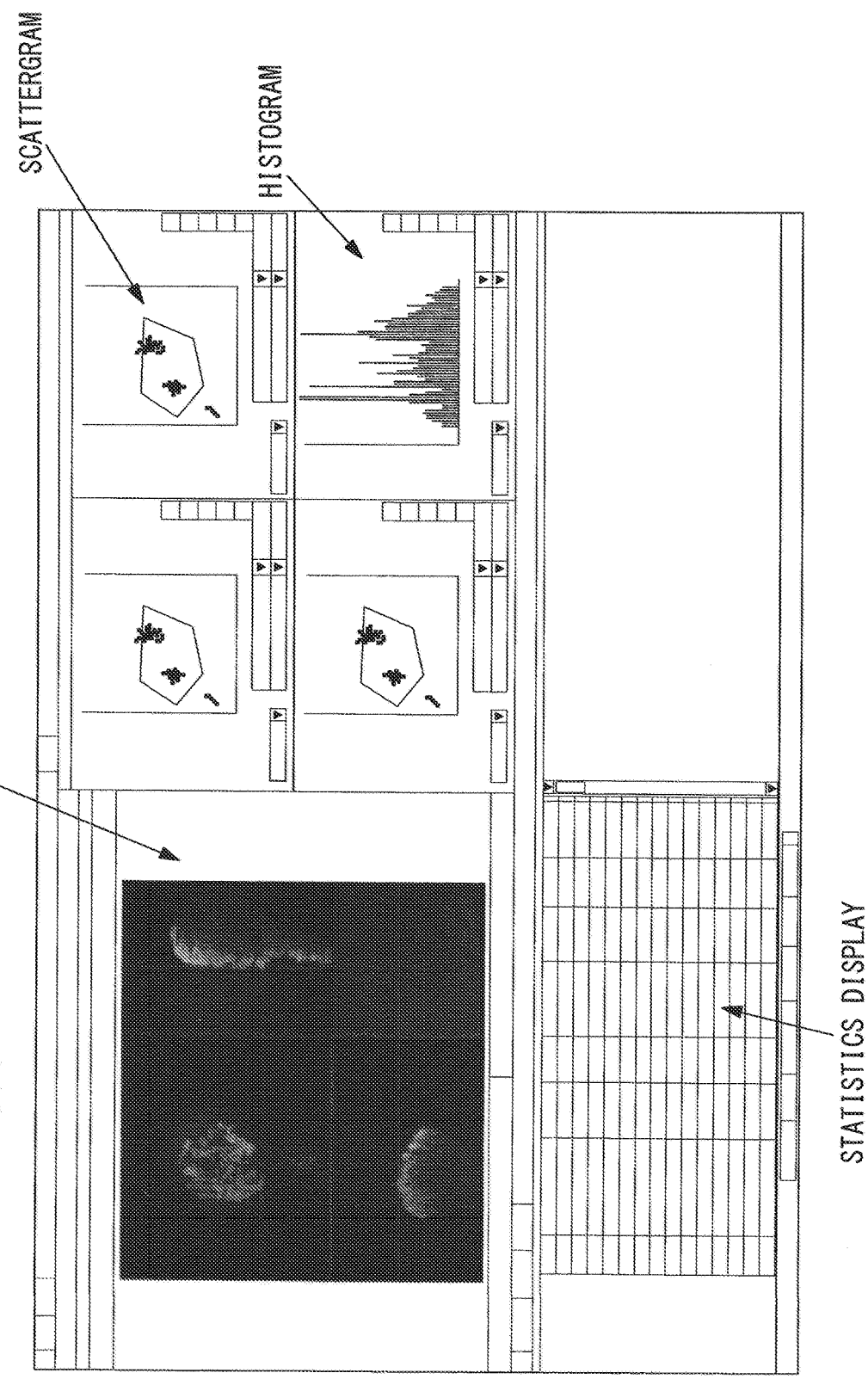
FIG. 5 is a view showing a state in which cross-sectional images and graphs are displayed next to one another on the monitor.

Furthermore, through execution of the display program, the CPU 71 associates three mutually orthogonal cross-sectional images that constitute a 3D image, i.e., an XY cross-sectional image, an XZ cross-sectional image, and a YZ cross-sectional image, and simultaneously displays the cross-sectional images on the monitor 7 (three-plane display), as shown in FIG. 4, for example. The respective cross-sectional images correspond to an image acquired in the XY direction and 2D images generated in cross section by cutting the 3D image in the XZ direction and the YZ direction. Furthermore, as shown in FIG. 5, the CPU 71 displays graphs, such as a histogram and a scattergram, indicating the characteristic distributions of the measured and analyzed cells S, on the monitor 7 next to the respective cross-sectional images.

Figure 6:
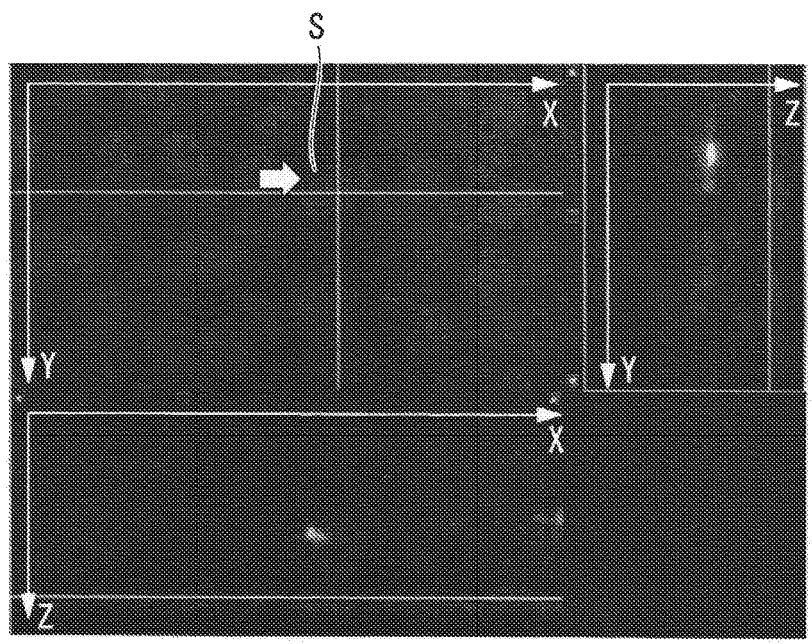
FIG. 6 is a view showing a state in which an arbitrary cell is specified by an arrow in the XY cross-sectional image.

Furthermore, for example, as shown in FIG. 6, when an operator specifies, with the input unit 11, an arbitrary cell S in any of the cross-sectional images and the graphs displayed on the monitor 7, the CPU 71 extracts, from the 3D image, the cross-sectional shapes of the specified cell S in the respective cross-sectional images on the basis of the label assigned to the cell S, synthesizes the cross-sectional shapes as recognized areas, and extracts, from the graphs stored in the memory 73, the analysis result of the specified cell S.

Figure 7:
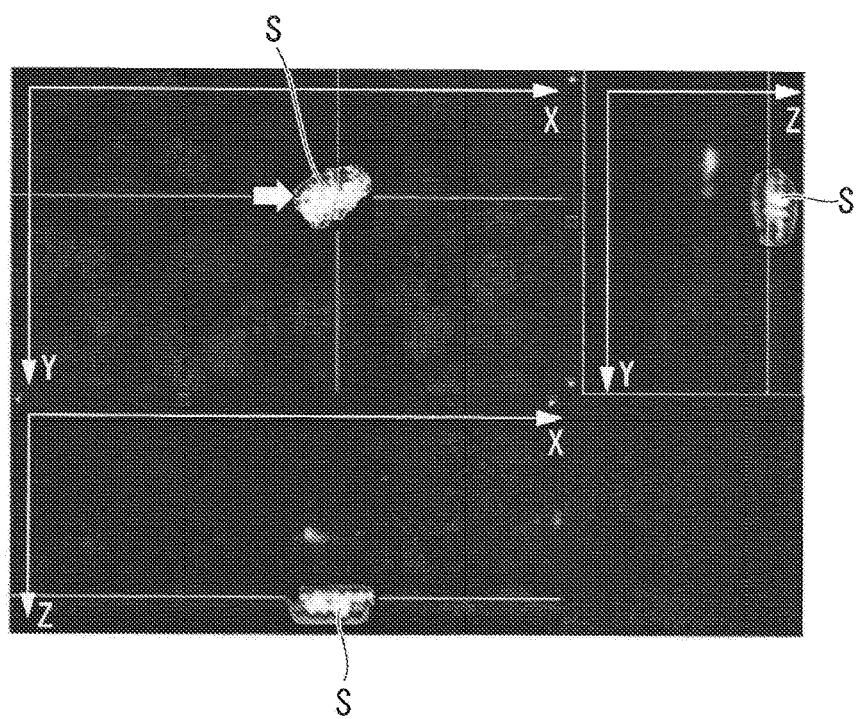
FIG. 7 is a view showing a state in which cross-sectional shapes of the cell specified in FIG. 6 are highlighted in the respective cross-sectional images.
Figure 8:
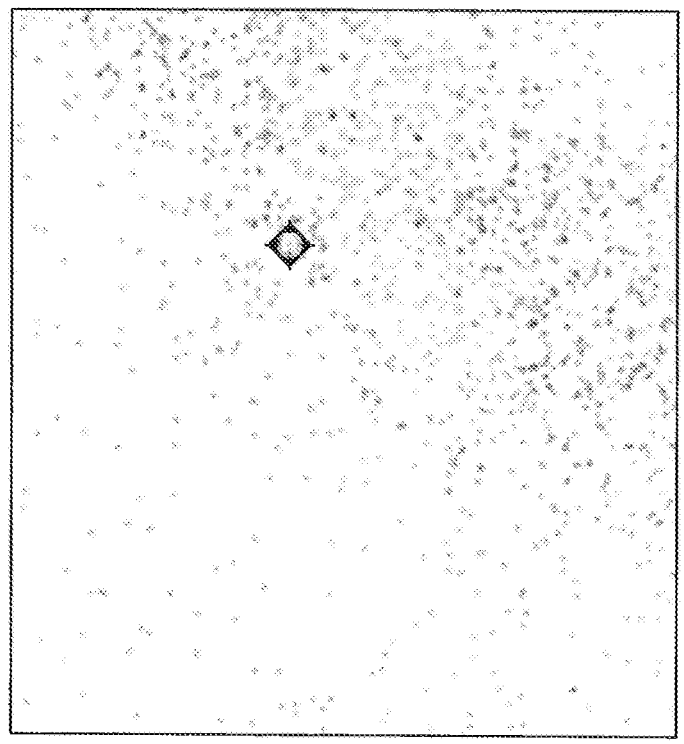
FIG. 8 is a view showing a state in which the value indicating an analysis result of the cell specified in FIG. 6 is highlighted in a graph.

Then, through execution of the display program, as shown in FIG. 7, the CPU 71 associates the synthesized cross-sectional shapes of the cell S with one another, superimposes them on the respective cross-sectional images on the monitor 7, and highlights them in a distinguishable manner from the other cells S. Furthermore, as shown in FIG. 8, the CPU 71 associates a value indicating the extracted analysis result of the cell S with the cross-sectional shapes highlighted in the cross-sectional images, thus highlighting the value in the graph on the monitor 7 in a distinguishable manner from the other cells S. The graph shown in FIG. 8 shows the relationship between the volume of the cell S and the sum of the luminance, as an example.

With the input unit 11, an arbitrary cell S can be specified in any of the cross-sectional images and the graphs displayed on the monitor 7. For example, FIG. 6 shows a state in which an arbitrary cell S is specified by an arrow in the XY cross-sectional image.

The operation of the thus-configured observation system 1 will now be described.

First, a description will be given of a case in which a 3D image of cells S is obtained by using the observation system 1 of this embodiment.

First, the sample holder 29 is made to hold the container, the container is mounted on the motorized stage 13, and laser light is emitted from the laser-light source unit 15.

The laser light emitted from the laser-light source unit 15 is two-dimensionally scanned by the scanner 17 and is focused on the cells S in the container via the pupil projection lens 47, the imaging lens 49, and the objective lens 19. At the position irradiated with the laser light, fluorescent substances existing in the cells S are excited, thus producing fluorescence. The produced fluorescence returns along the light path of the laser light via the objective lens 19, the imaging lens 49, the pupil projection lens 47, and the scanner 17, is split off by the beam splitter 51, and enters the image acquisition unit 21.

The fluorescence entering the image acquisition unit 21 is focused by the confocal lens 53, and only fluorescence passing through the variable pinhole 55 is substantially collimated by the collimating lens 57, is then separated by the grating 59, and is detected by the different light detectors 65 for respective wavelengths, via the condensing lens 61 and the beam splitter 63. Then, the control device 5 constructs a slice image of the cells S on the basis of the luminance signals output from the light detectors 65, and subjects a plurality of constructed slice images to image processing, thus constructing a 3D image.

In this case, the variable pinhole 55 is sufficiently reduced, thereby making it possible to cause only fluorescence produced at the focus position of the objective lens 19 to pass therethrough, to detect the fluorescence at the light detectors 65, and to acquire a clear confocal fluorescence image.

Figure 9:
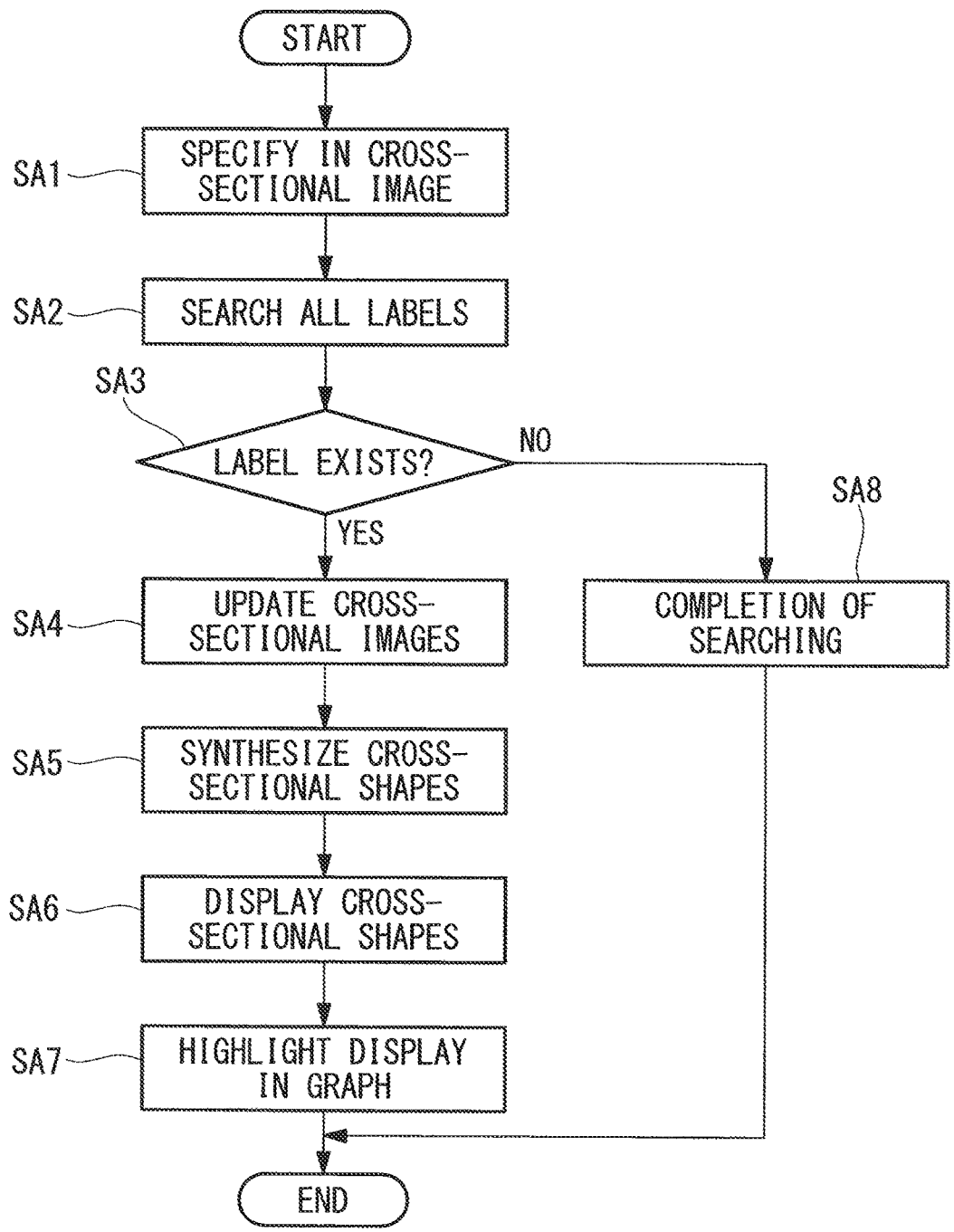
FIG. 9 is a flowchart for explaining the process for highlighting a desired cell by using the observation system shown in FIG. 1.

Next, a description will be given of a case in which a desired cell S is highlighted by using the observation system 1 of this embodiment with reference to the flowchart shown in FIG. 9.

First, the CPU 71 executes the recognition program, recognizes individual cells S in a 3D image stored in the disk 69, identifies the cells by assigning, thereto, labels that differ from one another, and generates a label image, such as that shown in FIG. 2, and a table, such as that shown in FIG. 3.

Furthermore, the CPU 71 executes the measurement program, measures and analyzes the individual cells S recognized from the 3D image, and generates graphs showing the characteristic distributions of the measured and analyzed cells S. Then, the CPU 71 executes the display program, associates the XY cross-sectional image, the XZ cross-sectional image, and the YZ cross-sectional image, which constitute the 3D image, and the graphs with one another, and displays them next to one another on the monitor 7.

Then, for example, as shown in FIG. 10, when the operator specifies, with the input unit 11, an arbitrary position in the XY cross-sectional image on the monitor 7 (Step SA1), the CPU 71 searches all labels in the label image and the table stored in the disk 69 (Step SA2).

If there is a label that includes the position in the XY cross-sectional image specified by the operator, i.e., if a cell S exists at the position specified in the XY cross-sectional image ("YES" in Step SA3), the CPU 71 updates the cross-sectional images on the monitor 7 so as to be centered on the specified XY-coordinates (Step SA4).

Then, the CPU 71 extracts, from the 3D image, the cross-sectional shapes, in the respective cross-sectional images, of the cell S that is assigned that label and synthesizes the cross-sectional shapes as recognized areas (Step SA5). Furthermore, the CPU 71 extracts, from the graphs, the analysis result of the cell S that is assigned that label.

Then, the CPU 71 executes the display program, and, as shown in FIG. 10, associates the synthesized cross-sectional shapes in the respective cross-sectional images with one another, and highlights them in the respective cross-sectional images on the monitor 7 in a distinguishable manner from the other cells S (Step SA6). Furthermore, as shown in FIG. 10, the CPU 71 associates the value indicating the extracted analysis result of the cell S with the cross-sectional shapes highlighted in the cross-sectional images and highlights the value in the graph on the monitor 7 in a distinguishable manner from the other cells S (Step SA7).

On the other hand, if there is no label that includes the position in the cross-sectional image specified by the operator, i.e., if no cell S exists at the position specified in the cross-sectional image ("NO" in Step SA3), searching performed by the CPU 71 is completed (Step SA8), and the processing flow ends.

Figure 11:
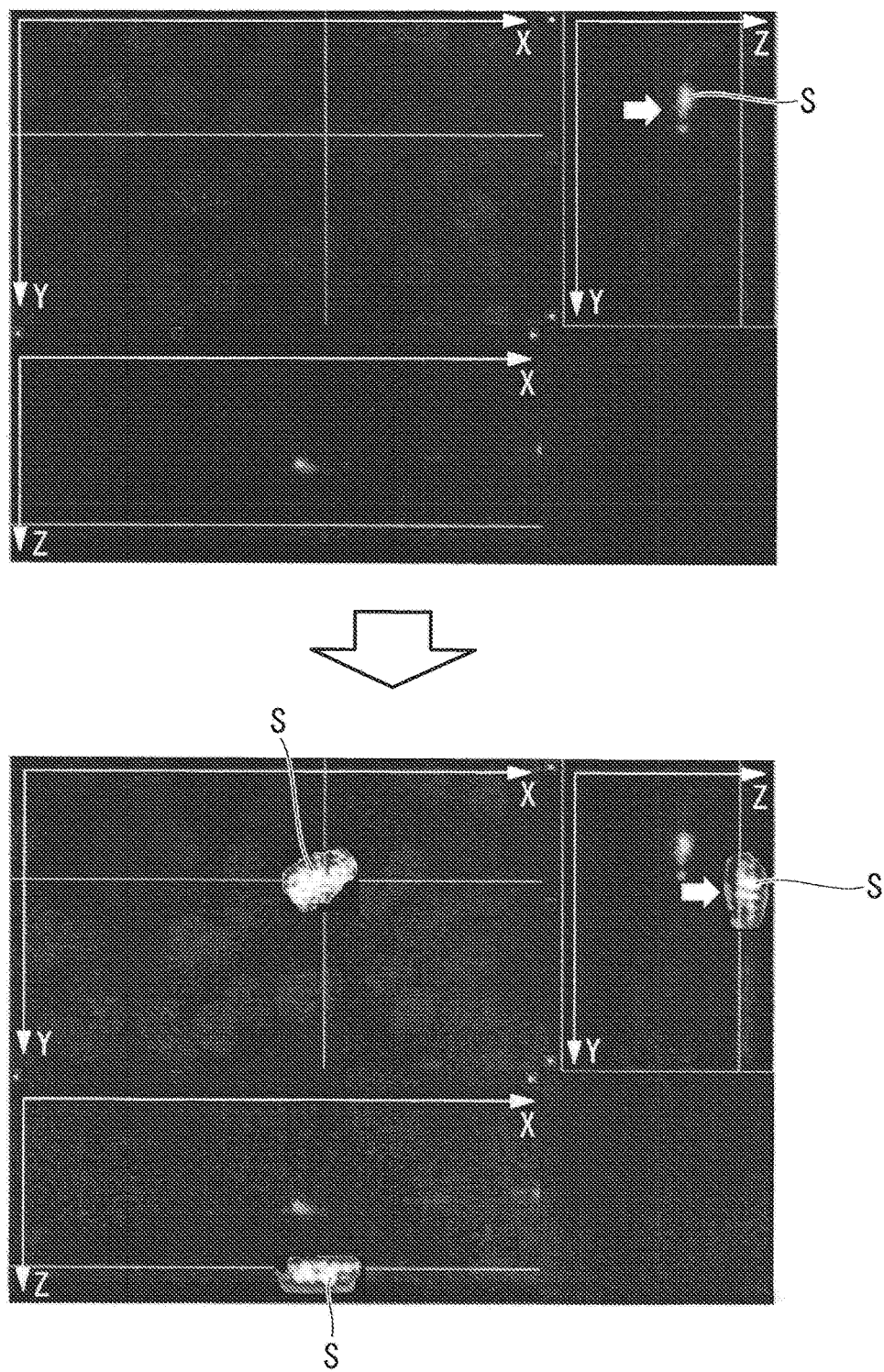
FIG. 11 is a view showing a state in which an arbitrary cell is specified in the YZ cross-sectional image, thereby highlighting the cross-sectional shapes of the cell in the respective cross-sectional images.

Similarly, for example, as shown in FIG. 11, when an arbitrary cell S is specified in the YZ cross-sectional image, the cross-sectional shapes of the specified cell S in the respective cross-sectional images and the analysis result thereof are extracted on the basis of the label assigned to the cell S, the synthesized cross-sectional shapes of the cell S are highlighted in the cross-sectional images, and a value indicating the analysis result of the cell S is highlighted in the graph. The same applies when an arbitrary cell S is specified in the XZ cross-sectional image. FIG. 11 does not show a state in which the value is highlighted in the graph.

Figure 12:
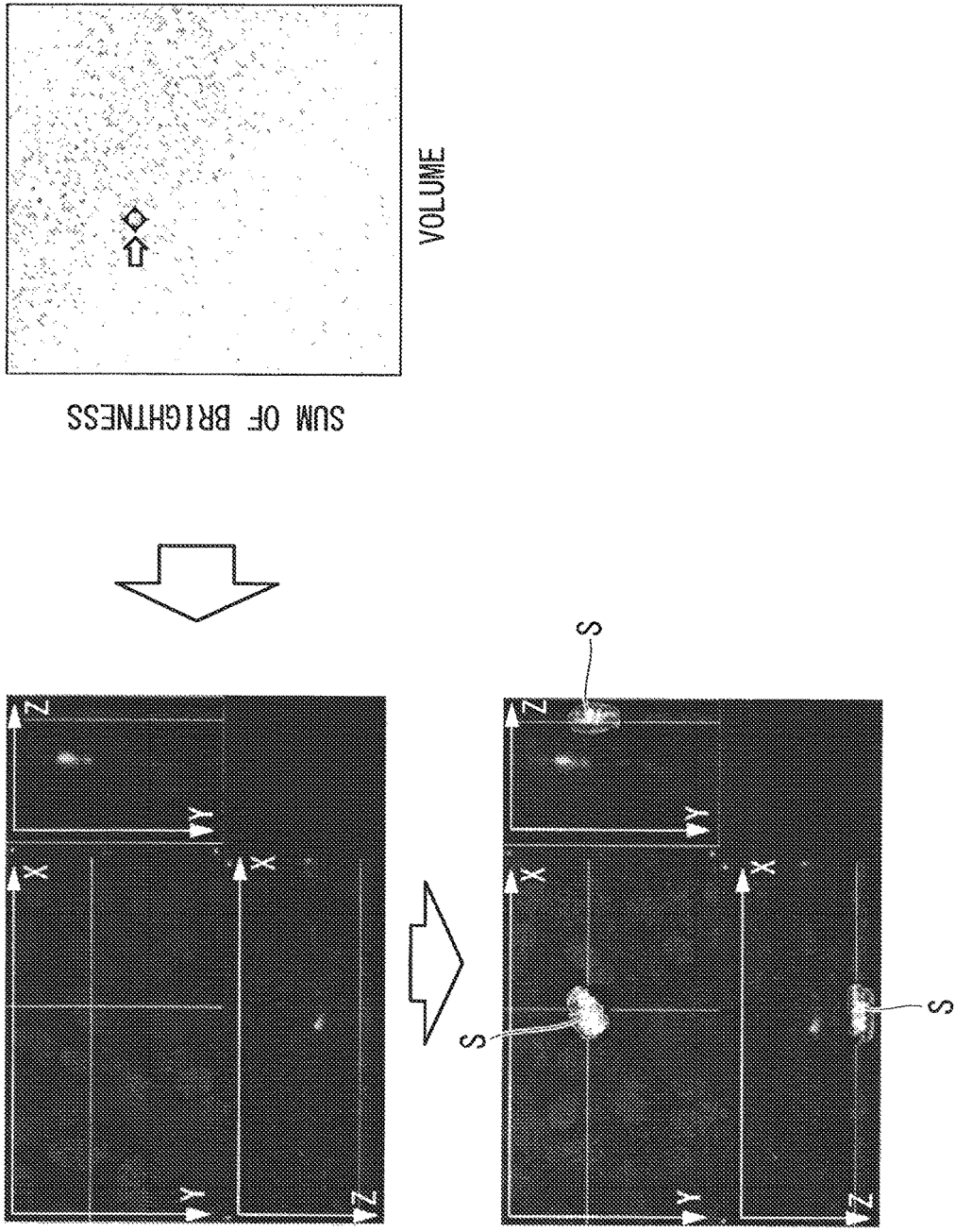
FIG. 12 is a view showing a state in which an arbitrary cell is specified in the graph, thereby updating the respective cross-sectional images so as to be centered on the cell and highlighting the cross-sectional shapes of the cell in the respective cross-sectional images.

Furthermore, similarly, for example, as shown in FIG. 12, when an arbitrary cell S is specified in the graph, the cross-sectional images on the monitor 7 are updated so as to be centered on the specified cell S. Then, the cross-sectional shapes of the specified cell S in the respective cross-sectional images and the analysis result thereof are extracted on the basis of the label assigned to the cell S, the value indicating the analysis result of the cell S is highlighted in the graph, and the cross-sectional shapes of the cell S are highlighted in the cross-sectional images.

As described above, according to the observation system 1 of this embodiment, the respective cross-sectional shapes of a desired cell S in three mutually-intersecting directions and the value indicating the analysis result thereof are highlighted in the three cross-sectional images and the graph, which are simultaneously displayed on the monitor 7, thereby allowing the operator to simultaneously and visibly recognize the cross-sectional shapes and the analysis result of the cell S. Accordingly, with respect to a collection of cells S having a 3D structure, the certainty of 3D recognition of an observation-target cell S can be visually verified with ease and accuracy, together with the analysis result thereof.

Figure 13:
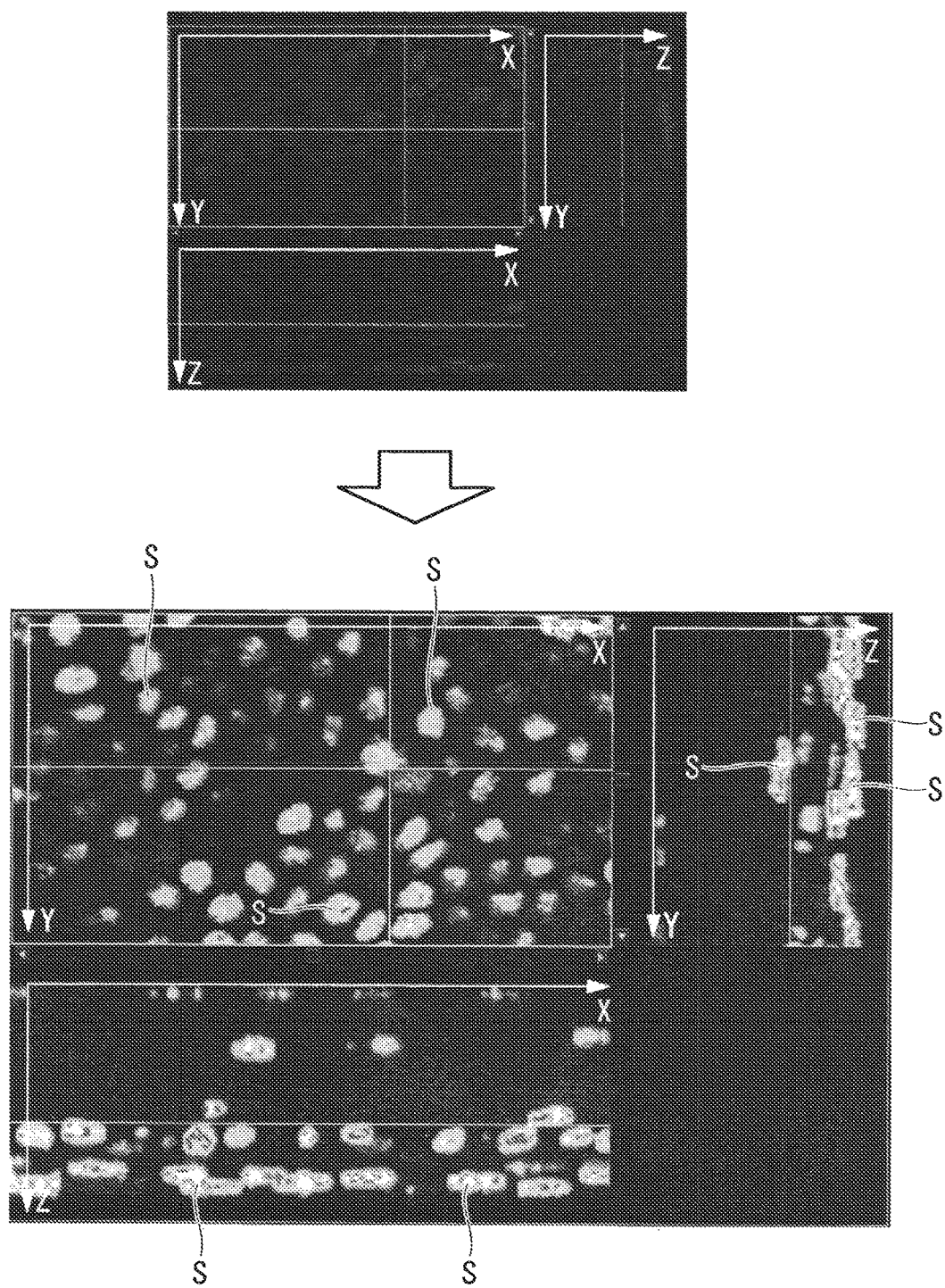
FIG. 13 is a view showing a state in which the respective cross-sectional shapes of all extracted cells are highlighted in the respective cross-sectional images.

In this embodiment, for example, when the operator specifies a plurality of positions using the input unit 11, as shown in FIG. 13, the CPU 71 may highlight the cross-sectional shapes of all extracted cells S in the respective cross-sectional images, in a distinguishable manner from the other cells S. Similarly, the CPU 71 may highlight the values indicating the analysis results of all extracted cells S in the graph, in a distinguishable manner from the other cells S. By doing so, the cross-sectional shapes of a plurality of desired cells S in three mutually-intersecting directions and the analysis results thereof can be easily and visibly recognized at the same time by means of the respective cross-sectional images and the graph.

Second Embodiment

Next, an observation system according to a second embodiment of the present invention will be described.

An observation system 1 of this embodiment differs from the first embodiment in that the CPU (3D-shape extracting unit) 71 extracts the 3D shape of a cell S specified by the operator and highlights the 3D shape thereof in a 3D image on the monitor 7 in a distinguishable manner from the other cells S.

Identical reference signs are assigned below to portions having configurations common to those in the observation system 1 of the first embodiment, and a description thereof will be omitted.

A 3D image, such as that shown in FIG. 14, is displayed on the monitor 7, next to cross-sectional images that constitute the 3D image and a graph that indicates an analysis result.

With the input unit 11, an arbitrary cell S can be specified in any of the cross-sectional images, the graph, and the 3D image displayed on the monitor 7.

The CPU 71 extracts, from the 3D image, the 3D shape of a cell S specified by the operator, on the basis of the label assigned to each cell S, and synthesizes the 3D shape as a recognized area. Furthermore, through execution of the display program, the CPU 71 associates the synthesized 3D shape of the cell S with the cross-sectional shapes to be highlighted in the respective cross-sectional images and the analysis result to be highlighted in the graph, superimposes the 3D shape on the 3D image displayed on the monitor 7, and highlights the 3D shape in a distinguishable manner from the other cells S.

The operation of the thus-configured observation system 1 will now be described.

Figure 15:
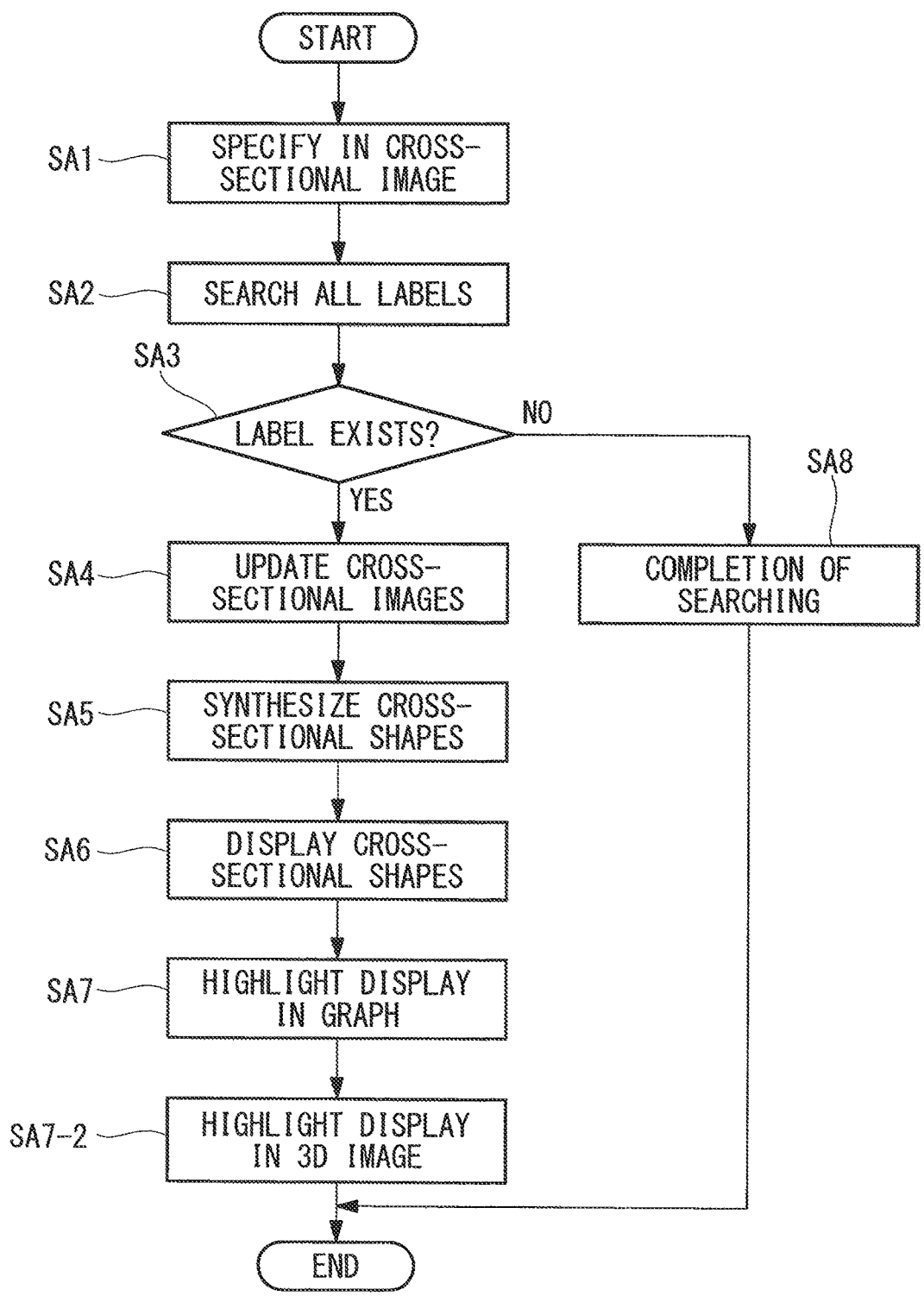
FIG. 15 is a flowchart for explaining the process for highlighting a desired cell by using the observation system according to the second embodiment of the present invention.

Since acquisition of a 3D image of cells S by using the observation system 1 of this embodiment is the same as that in the first embodiment, a description thereof will be omitted, and a case in which a desired cell S is highlighted will be described with reference to the flowchart shown in FIG. 15.

First, the CPU 71 executes the recognition program, recognizes individual cells S in a 3D image stored in the disk

69, identifies the cells S by assigning, thereto, labels that differ from one another, and generates a label image and a table.

Furthermore, the CPU 71 executes the measurement program, measures and analyzes the individual cells S recognized from the 3D image, and generates graphs showing the characteristic distributions of the measured and analyzed cells S. Then, the CPU 71 executes the display program, associates the 3D image, the XY cross-sectional image, the XZ cross-sectional image, the YZ cross-sectional image, and the graphs with one another, and displays them next to one another on the monitor 7.

Then, when an arbitrary position is specified in the XY cross-sectional image on the monitor 7, the label including that position is found, and the cross-sectional images on the monitor 7 are updated so as to be centered on the specified position (Step SA1 to Step SA4), the CPU 71 extracts, from the 3D image, the cross-sectional shapes, in the respective cross-sectional images, of the cell S that is assigned that label and synthesizes the cross-sectional shapes as recognized areas (Step SA5). Furthermore, the CPU 71 extracts, from the graph, the analysis result of the cell S that is assigned that label, extracts, from the 3D image, the 3D shape of the cell S, and synthesizes the 3D shape as a recognized area.

Then, the CPU 71 associates the synthesized cross-sectional shapes and 3D shape of the cell S and the extracted analysis result of the cell S with one another, highlights the cross-sectional shapes of the cell S and the value indicating the analysis result thereof in the cross-sectional images and the graph on the monitor 7 in a distinguishable manner from the other cells S (Step SA6 and Step SA7), and highlights the 3D shape of the cell S in the 3D image on the monitor 7 in a distinguishable manner from the other cells S (Step SA7-2), as shown in FIG. 16.

Similarly, when an arbitrary cell S is specified in the YZ cross-sectional image or the XZ cross-sectional image or when an arbitrary cell S is specified in the graph, the cross-sectional shapes in the cross-sectional images, the analysis result, and the 3D shape of the specified cell S are extracted on the basis of the label assigned to the cell S, and the cross-sectional shapes of the cell S, the value indicating the analysis result thereof, and the 3D shape thereof are highlighted in the cross-sectional images, in the graph, and in the 3D image, respectively.

Figure 17:
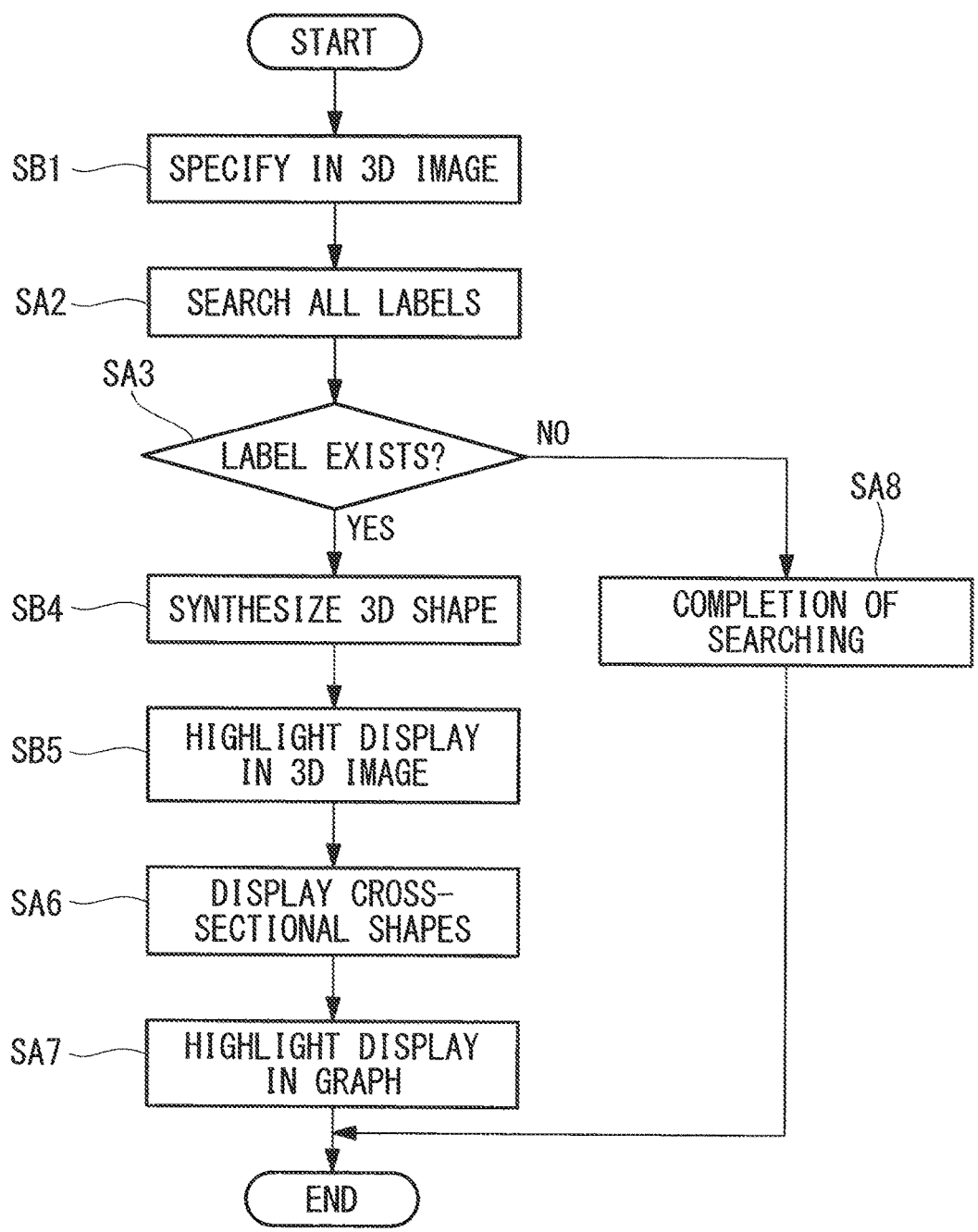
FIG. 17 is a flowchart for explaining another process for highlighting a desired cell by using an observation system according to a modification of the second embodiment of the present invention.

Furthermore, the same applies to a case in which an arbitrary cell S is specified in the 3D image on the monitor 7. For example, as in the flowchart shown in FIG. 17 and as shown in FIG. 18, when the operator specifies an arbitrary position in the 3D image on the monitor 7 by using the input unit 11 (Step SB1), the CPU 71 searches all labels in the label image and the table stored in the disk 69 (Step SA2). In this case, if it is in a Bounding Box of the cell S (in a circumscribed cube), it may be assumed to be a specified state.

If there is a label including the position in the 3D image specified by the operator, i.e., if a cell S exists at the position specified in the 3D image ("YES" in Step SA3), the CPU 71 updates the cross-sectional images on the monitor 7 so as to be centered on the specified XYZ-coordinates.

Then, the CPU 71 extracts, from the 3D image, the 3D shape of the cell S that is assigned that label and synthesizes the 3D shape as a recognized area (Step SB4). Furthermore, the CPU 71 extracts, from the 3D image, the cross-sectional shapes, in the respective cross-sectional images, of the cell S that is assigned that label, synthesizes the cross-sectional shapes as recognized areas, and extracts, from the graph, the analysis result of the cell S that is assigned that label.

Then, the CPU 71 associates the synthesized 3D shape, the synthesized respective cross-sectional shapes, and the extracted analysis result with one another, superimposes the 3D shape of the cell S on the 3D image on the monitor 7, and highlights the 3D shape in a distinguishable manner from the other cells S (Step SB5), as shown in FIG. 18. Furthermore, the CPU 71 highlights the respective cross-sectional shapes of the cell S and the value indicating the analysis result thereof in the respective cross-sectional images and the graph on the monitor 7 in a distinguishable manner from the other cells S (Step SA6 and Step SA7). In this case, if a plurality of cells S exist in the depth direction of the specified position in the 3D image, a cell S that exists at the frontmost position is assumed to be selected, and the cell S is highlighted.

As described above, according to the observation system 1 of this embodiment, the respective cross-sectional shapes of a desired cell S in three mutually-intersecting directions, the value indicating the analysis result thereof, and the 3D shape thereof are highlighted in the three cross-sectional images, the graph, and the 3D image displayed on the monitor 7, thereby allowing the operator to visibly recognize the respective cross-sectional shapes of the cell S in three mutually-intersecting directions, the analysis result thereof, and the 3D shape thereof, in association with one another. Accordingly, with respect to a collection of cells S having a 3D structure, the certainty of 3D recognition of an observation-target cell S can be visually verified with ease and accuracy.

Figure 19:
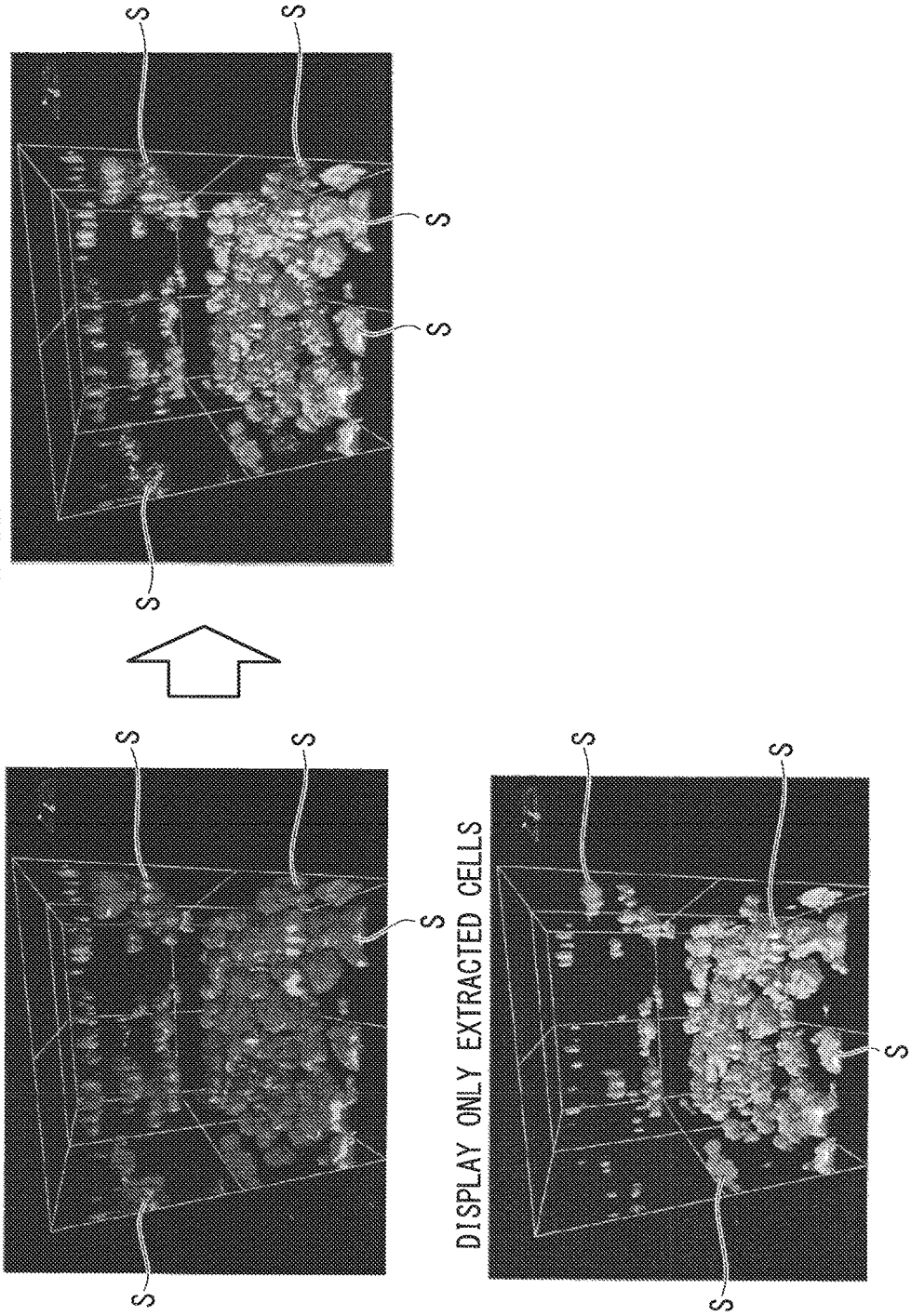
FIG. 19 is a view showing a state in which the 3D shapes of all cells are displayed in the 3D image, a state in which only the 3D shapes of extracted cells are displayed in the 3D image, and a state in which the 3D shapes of the extracted cells are highlighted in the 3D image in which the 3D shapes of all cells have been displayed.

In this embodiment, for example, when the operator specifies a plurality of positions by using the input unit 11, as shown in FIG. 19, instead of displaying all cells S in the 3D image, the CPU 71 may display only the 3D shapes of all extracted cells S in the 3D image or may display all cells S, then, may superimpose the 3D shapes of all extracted cells S on the 3D shapes of the corresponding cells S, and may highlight the 3D shapes of all extracted cells S. By doing so, the 3D shapes of a plurality of desired cells S can be easily and visibly recognized at the same time by means of a 3D image.

Although the embodiments of the present invention have been described above in detail with reference to the drawings, the specific configurations are not limited to the embodiments, and design changes etc. that do not depart from the scope of the present invention are also encompassed. For example, the present invention is not limited to those applied to the above-described embodiments, can be applied to an embodiment obtained by appropriately combining these embodiments, and is not particularly limited.

Figure 20:
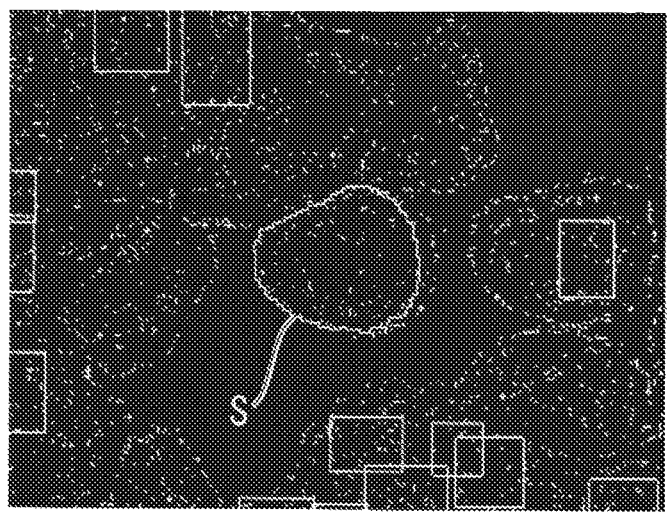
FIG. 20 is a view showing a state in which only outlines of the cross-sectional shapes of extracted cells are highlighted in a cross-sectional image.

Furthermore, in this embodiment, although, when the cross-sectional shapes of an extracted cell S are highlighted, the entire cross-sectional shapes of the cell S are displayed in the cross-sectional images in a brighter manner than the cross-sectional shapes of the other cells S, instead of this, for example, as shown in FIG. 20, it is also possible to display, in the cross-sectional images, only the outlines of the cross-sectional shapes of the cell S in a brighter manner than the outlines of the cross-sectional shapes of the other cells S. The same applies to the 3D shape of the cell S.

From the above-described embodiments and modifications thereof, the following aspects of the invention are derived.

According to one aspect, the present invention provides an observation system including: a display unit that displays an image of cells; a cell identifying unit that identifies, in a 3D image including the plurality of cells, the respective cells by assigning labels that differ from one another to the respective cells; a display control unit that associates three mutually-intersecting cross-sectional images that constitute the 3D image and that simultaneously displays the cross-sectional images on the display unit; a cell specifying unit with which an operator specifies an arbitrary one of the cells in any of the cross-sectional images, which are displayed on the display unit by the display control unit; and a cross-sectional-shape extracting unit that extracts, from the 3D image, cross-sectional shapes, in the respective cross-sectional images, of the cell specified by using the cell specifying unit, on the basis of the labels assigned to the respective cells, wherein the display control unit associates the cross-sectional shapes of the cell, which are extracted by the cross-sectional-shape extracting unit, with one another and displays the cross-sectional shapes of the cell in the respective cross-sectional images displayed on the display unit, in a distinguishable manner from the other cells.

According to this aspect, the cell identifying unit identifies a plurality of cells in a 3D image by assigning, thereto, labels that differ from one another, and the display control unit simultaneously displays, on the display unit, three mutually-intersecting cross-sectional images of the 3D image. Then, when the operator specifies an arbitrary cell in any of the cross-sectional images displayed on the display unit, by using the cell specifying unit, the cross-sectional-shape extracting unit extracts, from the 3D image, the cross-sectional shapes of the specified cell in the respective cross-sectional images, on the basis of the labels assigned to the respective cells, associates the extracted cross-sectional shapes with one another, and displays the extracted cross-sectional shapes in the respective cross-sectional images displayed on the display unit, in a distinguishable manner from the other cells.

Therefore, the operator can simultaneously and visibly recognize the respective cross-sectional shapes of a desired cell in three mutually-intersecting directions, by means of the three cross-sectional images simultaneously displayed on the display unit. Accordingly, with respect to a collection of cells having a 3D structure, the certainty of 3D recognition of an observation-target cell can be visually verified with ease and accuracy.

In the above-described aspect, the display control unit may display the respective cross-sectional shapes of one or more of the cells, which are extracted by the cross-sectional-shape extracting unit, in the respective cross-sectional images in a distinguishable manner from the other cells.

With this configuration, the cross-sectional shapes of one or more cells of interest in three mutually-intersecting directions can be easily and visibly recognized by means of the respective cross-sectional images. When the respective cross-sectional shapes of a plurality of cells are displayed in the respective cross-sectional images in a distinguishable manner from the other cells, the certainty of 3D recognition of the plurality of cells can be easily verified at one time.

In the above-described aspect, the cell specifying unit may be capable of being used to specify an arbitrary one of the cells in any of the three cross-sectional images; and the display control unit may display the respective cross-sectional shapes of the cell, which are extracted by the cross-sectional-shape extracting unit, in all of the cross-sectional images, which include the cross-sectional image in which the cell is specified by using the cell specifying unit, in a distinguishable manner from the other cells.

With this configuration, the operator can specify a cell to be focused on from any of the three mutually-intersecting cross-sectional images, which constitute the 3D image, and to easily and visibly recognize the cross-sectional shapes of the cell in three mutually-intersecting directions by means of the respective cross-sectional images.

The above-described aspect may further include an analysis-result extracting unit that extracts, from the 3D image, an analysis result of the cell specified by using the cell specifying unit, on the basis of the labels assigned to the respective cells, wherein the display unit may display a graph that indicates the analysis result of the cell; and the display control unit may associate the analysis result of the cell, which is extracted by the analysis-result extracting unit, with the respective cross-sectional shapes to be displayed in the respective cross-sectional images in a distinguishable manner from the other cells and may display the analysis result of the cell in the graph displayed on the display unit, in a distinguishable manner from the other cells.

With this configuration, when the operator specifies an arbitrary cell in any of the cross-sectional images displayed on the display unit, by using the cell specifying unit, the analysis-result extracting unit extracts, from the 3D image, an analysis result of the specified cell on the basis of the labels assigned to the respective cells, associates the extracted analysis result with the respective cross-sectional shapes in the respective cross-sectional images, and displays the extracted analysis result in the graph displayed on the display unit, in a distinguishable manner from the other cells.

Therefore, the operator can visibly recognize the respective cross-sectional shapes of the desired cell in the three mutually-intersecting directions and the analysis result thereof, in association with one another, by means of the three cross-sectional images and the graph displayed on the display unit. Accordingly, with respect to a collection of cells having a 3D structure, the certainty of 3D recognition of an observation-target cell can be visually verified with ease and accuracy, together with the analysis result.

In the above-described aspect, the display control unit may display the analysis result of one or more of the cells, which is extracted by the analysis-result extracting unit, in the graph in a distinguishable manner from the other cells.

With this configuration, the analysis result of one or more cells of interest can be easily and visibly recognized by means of the graph. When the analysis results of a plurality of cells are displayed in the graph in a distinguishable manner from the other cells, the certainty of 3D recognition of the plurality of cells can be easily verified at one time, together with the analysis results.

In the above-described aspect, the cell specifying unit may be capable of being used to specify an arbitrary one of the cells in any of the three cross-sectional images and the graph; and the display control unit may display the cross-sectional shapes of the cell, which are extracted by the cross-sectional-shape extracting unit, and the analysis result of the cell, which is extracted by the analysis-result extracting unit, in all of the cross-sectional images and the graph, which include the cross-sectional image or the graph in which the cell is specified by using the cell specifying unit, in a distinguishable manner from the other cells.

With this configuration, the operator can specify a cell to be focused on from any of the three mutually-intersecting cross-sectional images, which constitute the 3D image, and the graph and can easily and visibly recognize the cross-sectional shapes of the cell in the three mutually-intersecting directions and the analysis result thereof by means of the respective cross-sectional images and the graph.

The above-described aspect may further include a 3D-shape extracting unit that extracts, from the 3D image, a 3D shape of the cell specified by using the cell specifying unit, on the basis of the labels assigned to the respective cells, wherein the display unit may display the 3D image; and the display control unit may associate the 3D shape of the cell, which is extracted by the 3D-shape extracting unit, with the cross-sectional shapes to be displayed in the respective cross-sectional images in a distinguishable manner from the other cells and may display the 3D shape of the cell in the 3D image displayed on the display unit, in a distinguishable manner from the other cells.

With this configuration, when the operator specifies an arbitrary cell in any of the cross-sectional images displayed on the display unit, by using the cell specifying unit, the 3D-shape extracting unit extracts, from the 3D image, the 3D shape of the specified cell on the basis of the labels assigned to the respective cells, associates the extracted 3D shape with the respective cross-sectional shapes in the respective cross-sectional images, and displays the extracted 3D shape in the 3D image displayed on the display unit, in a distinguishable manner from the other cells.

Therefore, the operator can visibly recognize the respective cross-sectional shapes of a desired cell in the three mutually-intersecting directions and the 3D shape thereof, in association with one another, by means of the three cross-sectional images and the 3D image displayed on the display unit. Accordingly, with respect to a collection of cells having a 3D structure, the certainty of 3D recognition of an observation-target cell can be visually verified with ease and accuracy.

In the above-described aspect, the display control unit may display the 3D shape of one or more of the cells, which is extracted by the 3D-shape extracting unit, in the 3D image in a distinguishable manner from the other cells.

With this configuration, the 3D shape of one or more cells of interest can be easily and visibly recognized by means of the 3D image. When the 3D shapes of a plurality of cells are displayed in the 3D image in a distinguishable manner from the other cells, the certainty of 3D recognition of the plurality of observation-target cells can be easily verified at one time.

In the above-described aspect, the cell specifying unit may be capable of being used to specify an arbitrary one of the cells in any of the three cross-sectional images and the 3D image; and the display control unit may display the cross-sectional shapes of the cell, which are extracted by the cross-sectional-shape extracting unit, and the 3D shape of the cell, which is extracted by the 3D-shape extracting unit, in all of the cross-sectional images and the 3D image, which include the cross-sectional image or the 3D image in which the cell is specified by using the cell specifying unit, in a distinguishable manner from the other cells.

With this configuration, the operator can specify a cell to be focused on from any of the three mutually-intersecting cross-sectional images, which constitute the 3D image, and the 3D image and can easily and visibly recognize the cross-sectional shapes of the cell in the three mutually-intersecting directions and the 3D shape thereof by means of the respective cross-sectional images and the 3D image.

The above-described aspect may further include: an analysis-result extracting unit that extracts, from the 3D image, an analysis result of the cell specified by using the cell specifying unit, on the basis of the labels assigned to the respective cells; and a 3D-shape extracting unit that extracts, from the 3D image, a 3D shape of the cell specified by using the cell specifying unit, on the basis of the labels assigned to the respective cells, wherein the display unit may display a graph that indicates the analysis result of the cell and the 3D image; and the display control unit may associate the analysis result of the cell, which is extracted by the analysis-result extracting unit, with the respective cross-sectional shapes to be displayed in the respective cross-sectional images in a distinguishable manner from the other cells, may display the analysis result of the cell in the graph displayed on the display unit, in a distinguishable manner from the other cells, and may display the 3D shape of the cell, which is extracted by the 3D-shape extracting unit, in the 3D image displayed on the display unit, in a distinguishable manner from the other cells.

With this configuration, when the operator specifies an arbitrary cell in any of the cross-sectional images displayed on the display unit, by using the cell specifying unit, the analysis-result extracting unit and the 3D-shape extracting unit extract, from the 3D image, the analysis result and the 3D shape of the specified cell on the basis of the labels assigned to the respective cells, associate the extracted analysis result and 3D shape with the respective cross-sectional shapes in the respective cross-sectional images, and display the analysis result and the 3D shape in the graph and the 3D image displayed on the display unit, in a distinguishable manner from the other cells.

Therefore, the operator can visibly recognize the respective cross-sectional shapes of a desired cell in the three mutually-intersecting directions, the analysis result thereof, and the 3D shape thereof, in association with one another, by means of the three cross-sectional images, the graph, and the 3D image, which are displayed on the display unit. Accordingly, with respect to a collection of cells having a 3D structure, the certainty of 3D recognition of an observation-target cell can be visually verified with ease and accuracy, together with the analysis result.

In the above-described aspect, the display control unit may display the analysis result of one or more of the cells, which is extracted by the analysis-result extracting unit, in the graph in a distinguishable manner from the other cells and may display the 3D shape of one or more of the cells, which is extracted by the 3D-shape extracting unit, in the 3D image in a distinguishable manner from the other cells.

With this configuration, the analysis result and the 3D shape of one or more cells of interest can be easily and visibly recognized by means of the graph and the 3D image. When the analysis results and the 3D shapes of a plurality of cells are displayed in the graph and the 3D image in a distinguishable manner from the other cells, the certainty of 3D recognition of the plurality of cells can be easily verified at one time, together with the analysis results.

In the above-described aspect, the cell specifying unit may be capable of being used to specify the cells in any of the three cross-sectional images, the graph, and the 3D image; and the display control unit may display the cross-sectional shapes of the cells, which are extracted by the cross-sectional-shape extracting unit, the analysis results of the cells, which are extracted by the analysis-result extracting unit, and the 3D shapes of the cells, which are extracted by the 3D-shape extracting unit, in all of the cross-sectional images, the graph, and the 3D image, which include the cross-sectional image, the graph, or the 3D image in which the cells are specified by using the cell specifying unit, in a distinguishable manner from the other cells.

With this configuration, the operator can specify a cell to be focused on from any of the three mutually-intersecting cross-sectional images, which constitute the 3D image, the graph, and the 3D image and can easily and visibly recognize the cross-sectional shapes of the cell in the three mutually-intersecting directions, the analysis result thereof, and the 3D shape thereof by means of the respective cross-sectional images, the graph, and the 3D image.

REFERENCE SIGNS LIST 1 observation system
7 monitor (display unit)
11 input unit (cell specifying unit)
71 CPU (cell identifying unit, display control unit, cross-sectional-shape extracting unit, analysis-result extracting unit, 3D-shape extracting unit)
S cell

The invention claimed is:

1. An observation system comprising:
a display unit that displays an image of a plurality of cells;
a cell identifying unit that identifies, in a 3D image including the plurality of cells, respective cells by assigning labels that differ from one another to the respective cells;
a display control unit that associates three mutually-intersecting cross-sectional images that constitute the 3D image and that simultaneously displays the cross-sectional images on the display unit;
a cell specifying unit with which an operator specifies an arbitrary cell in any of the cross-sectional images, which are displayed on the display unit by the display control unit; and
a cross-sectional-shape extracting unit that extracts, from the 3D image, cross-sectional shapes, in the respective cross-sectional images, of the cell specified by using the cell specifying unit, on the basis of the labels assigned to the respective cells,
wherein the display control unit associates the cross-sectional shapes of the cell, which are extracted by the cross-sectional-shape extracting unit, with one another and displays the cross-sectional shapes of the cell in the respective cross-sectional images displayed on the display unit, in a distinguishable manner from the other cells.

2. The observation system according to claim 1, wherein the display control unit displays the respective cross-sectional shapes of at least one cell, which are extracted by the cross-sectional-shape extracting unit, in the respective cross-sectional images in a distinguishable manner from the other cells.

3. The observation system according to claim 1, wherein:
the cell specifying unit can be used to specify an arbitrary cell in any of the three cross-sectional images; and
the display control unit displays the respective cross-sectional shapes of the cell, which are extracted by the cross-sectional-shape extracting unit, in all of the cross-sectional images, which include the cross-sectional image in which the cell is specified by using the cell specifying unit, in a distinguishable manner from the other cells.

4. The observation system according to claim 1, further comprising an analysis-result extracting unit that extracts, from the 3D image, an analysis result of the cell specified by the cell specifying unit, on the basis of the labels assigned to the respective cells,
wherein:
the display unit displays a graph that indicates the analysis result of the cell; and
the display control unit associates the analysis result of the cell, which is extracted by the analysis-result extracting unit, with the respective cross-sectional shapes to be displayed in the respective cross-sectional images in a distinguishable manner from the other cells and displays the analysis result of the cell in the graph displayed on the display unit, in a distinguishable manner from the other cells.

5. The observation system according to claim 4, wherein the display control unit displays the analysis result of at least one cell, which is extracted by the analysis-result extracting unit, in the graph in a distinguishable manner from the other cells.

6. The observation system according to claim 4, wherein:
the cell specifying unit can be used to specify an arbitrary cell in any of the three cross-sectional images and the graph; and
the display control unit displays the cross-sectional shapes of the cell, which are extracted by the cross-sectional-shape extracting unit, and the analysis result of the cell, which is extracted by the analysis-result extracting unit, in all of the cross-sectional images and the graph, which include the cross-sectional image or the graph in which the cell is specified by using the cell specifying unit, in a distinguishable manner from the other cells.

7. The observation system according to claim 1, further comprising a 3D-shape extracting unit that extracts, from the 3D image, a 3D shape of the cell specified by using the cell specifying unit, on the basis of the labels assigned to the respective cells,
wherein:
the display unit displays the 3D image; and
the display control unit associates the 3D shape of the cell, which is extracted by the 3D-shape extracting unit, with the cross-sectional shapes to be displayed in the respective cross-sectional images in a distinguishable manner from the other cells and displays the 3D shape of the cell in the 3D image displayed on the display unit, in a distinguishable manner from the other cells.

8. The observation system according to claim 7, wherein the display control unit displays the 3D shape of at least one cell, which is extracted by the 3D-shape extracting unit, in the 3D image in a distinguishable manner from the other cells.

9. The observation system according to claim 7, wherein:
the cell specifying unit can be used to specify an arbitrary cell in any of the three cross-sectional images and the 3D image; and
the display control unit displays the cross-sectional shapes of the cell, which are extracted by the cross-sectional-shape extracting unit, and the 3D shape of the cell, which is extracted by the 3D-shape extracting unit, in all of the cross-sectional images and the 3D image, which include the cross-sectional image or the 3D image in which the cell is specified by using the cell specifying unit, in a distinguishable manner from the other cells.

10. The observation system according to claim 1, further comprising:
an analysis-result extracting unit that extracts, from the 3D image, an analysis result of the cell specified by using the cell specifying unit, on the basis of the labels assigned to the respective cells; and
a 3D-shape extracting unit that extracts, from the 3D image, a 3D shape of the cell specified by using the cell specifying unit, on the basis of the labels assigned to the respective cells,
wherein:

the display unit displays a graph that indicates the analysis result of the cell and the 3D image; and the display control unit associates the analysis result of the cell, which is extracted by the analysis-result extracting unit, with the respective cross-sectional shapes to be displayed in the respective cross-sectional images in a distinguishable manner from the other cells, displays the analysis result of the cell in the graph displayed on the display unit, in a distinguishable manner from the other cells, and displays the 3D shape of the cell, which is extracted by the 3D-shape extracting unit, in the 3D image displayed on the display unit, in a distinguishable manner from the other cells.

11. The observation system according to claim 10, wherein the display control unit displays the analysis result of at least one cell, which is extracted by the analysis-result extracting unit, in the graph in a distinguishable manner from the other cells and displays the 3D shape of at least one cell, which is extracted by the 3D-shape extracting unit, in the 3D image in a distinguishable manner from the other cells.

12. The observation system according to claim 10, wherein:

the cell specifying unit can be used to specify the cells in any of the three cross-sectional images, the graph, and the 3D image; and the display control unit displays the cross-sectional shapes of the cells, which are extracted by the cross-sectional-shape extracting unit, the analysis results of the cells, which are extracted by the analysis-result extracting unit, and the 3D shapes of the cells, which are extracted by the 3D-shape extracting unit, in all of the cross-sectional images, the graph, and the 3D image, which include the cross-sectional image, the graph, or the 3D image in which the cells are specified by using the cell specifying unit, in a distinguishable manner from the other cells.

13. The observation system according to claim 2, wherein:

the cell specifying unit can be used to specify an arbitrary cell in any of the three cross-sectional images; and the display control unit displays the respective cross-sectional shapes of the cell, which are extracted by the cross-sectional-shape extracting unit, in all of the cross-sectional images, which include the cross-sectional image in which the cell is specified by using the cell specifying unit, in a distinguishable manner from the other cells.

14. The observation system according to claim 2, further comprising an analysis-result extracting unit that extracts, from the 3D image, an analysis result of the cell specified by the cell specifying unit, on the basis of the labels assigned to the respective cells, wherein:

the display unit displays a graph that indicates the analysis result of the cell; and the display control unit associates the analysis result of the cell, which is extracted by the analysis-result extracting unit, with the respective cross-sectional shapes to be displayed in the respective cross-sectional images in a distinguishable manner from the other cells and displays the analysis result of the cell in the graph displayed on the display unit, in a distinguishable manner from the other cells.

15. The observation system according to claim 3, further comprising an analysis-result extracting unit that extracts, from the 3D image, an analysis result of the cell specified by the cell specifying unit, on the basis of the labels assigned to the respective cells, wherein:

the display unit displays a graph that indicates the analysis result of the cell; and the display control unit associates the analysis result of the cell, which is extracted by the analysis-result extracting unit, with the respective cross-sectional shapes to be displayed in the respective cross-sectional images in a distinguishable manner from the other cells and displays the analysis result of the cell in the graph displayed on the display unit, in a distinguishable manner from the other cells.

16. The observation system according to claim 5, wherein:

the cell specifying unit can be used to specify an arbitrary cell in any of the three cross-sectional images and the graph; and the display control unit displays the cross-sectional shapes of the cell, which are extracted by the cross-sectional-shape extracting unit, and the analysis result of the cell, which is extracted by the analysis-result extracting unit, in all of the cross-sectional images and the graph, which include the cross-sectional image or the graph in which the cell is specified by using the cell specifying unit, in a distinguishable manner from the other cells.

17. The observation system according to claim 2, further comprising a 3D-shape extracting unit that extracts, from the 3D image, a 3D shape of the cell specified by using the cell specifying unit, on the basis of the labels assigned to the respective cells, wherein:

the display unit displays the 3D image; and the display control unit associates the 3D shape of the cell, which is extracted by the 3D-shape extracting unit, with the cross-sectional shapes to be displayed in the respective cross-sectional images in a distinguishable manner from the other cells and displays the 3D shape of the cell in the 3D image displayed on the display unit, in a distinguishable manner from the other cells.

18. The observation system according to claim 3, further comprising a 3D-shape extracting unit that extracts, from the 3D image, a 3D shape of the cell specified by using the cell specifying unit, on the basis of the labels assigned to the respective cells, wherein:

the display unit displays the 3D image; and the display control unit associates the 3D shape of the cell, which is extracted by the 3D-shape extracting unit, with the cross-sectional shapes to be displayed in the respective cross-sectional images in a distinguishable manner from the other cells and displays the 3D shape of the cell in the 3D image displayed on the display unit, in a distinguishable manner from the other cells.

19. The observation system according to claim 2, further comprising:

an analysis-result extracting unit that extracts, from the 3D image, an analysis result of the cell specified by using the cell specifying unit, on the basis of the labels assigned to the respective cells; and a 3D-shape extracting unit that extracts, from the 3D image, a 3D shape of the cell specified by using the cell specifying unit, on the basis of the labels assigned to the respective cells, wherein:

the display unit displays a graph that indicates the analysis result of the cell and the 3D image; and the display control unit associates the analysis result of the cell, which is extracted by the analysis-result extracting unit, with the respective cross-sectional shapes to be displayed in the respective cross-sectional images in a distinguishable manner from the other cells, displays the analysis result of the cell in the graph displayed on the display unit, in a distinguishable manner from the other cells, and displays the 3D shape of the cell, which is extracted by the 3D-shape extracting unit, in the 3D image displayed on the display unit, in a distinguishable manner from the other cells.

20. The observation system according to claim 3, further comprising:

an analysis-result extracting unit that extracts, from the 3D image, an analysis result of the cell specified by using the cell specifying unit, on the basis of the labels assigned to the respective cells; and a 3D-shape extracting unit that extracts, from the 3D image, a 3D shape of the cell specified by using the cell specifying unit, on the basis of the labels assigned to the respective cells, wherein:

the display unit displays a graph that indicates the analysis result of the cell and the 3D image; and the display control unit associates the analysis result of the cell, which is extracted by the analysis-result extracting unit, with the respective cross-sectional shapes to be displayed in the respective cross-sectional images in a distinguishable manner from the other cells, displays the analysis result of the cell in the graph displayed on the display unit, in a distinguishable manner from the other cells, and displays the 3D shape of the cell, which is extracted by the 3D-shape extracting unit, in the 3D image displayed on the display unit, in a distinguishable manner from the other cells.

* * * * *